United States Patent
Putkaradze et al.

(10) Patent No.: US 12,123,828 B2
(45) Date of Patent: Oct. 22, 2024

(54) OLFACTORY SENSOR DEVICES AND RELATED METHODS

(71) Applicant: Olfato Wearables Limited, Alberta (CA)

(72) Inventors: Vakhtang Putkaradze, Calgary (CA); Natasa Vretenar, Calgary (CA); Josef Hocher, Calgary (CA); Keith Mertens, Oakland, CA (US)

(73) Assignee: OLFATO WEARABLES LIMITED, Alterta (CA)

( * ) Notice: Subject to any disclaimer, the term of this patent is extended or adjusted under 35 U.S.C. 154(b) by 288 days.

(21) Appl. No.: 17/523,739

(22) Filed: Nov. 10, 2021

(65) Prior Publication Data

US 2022/0146415 A1 May 12, 2022

Related U.S. Application Data

(60) Provisional application No. 63/112,394, filed on Nov. 11, 2020.

(51) Int. Cl.
  *G01N 21/3504* (2014.01)
  *G01N 33/00* (2006.01)
(52) U.S. Cl.
  CPC ..... *G01N 21/3504* (2013.01); *G01N 33/0001* (2013.01)
(58) Field of Classification Search
  CPC .................... G01N 21/3504; G01N 33/00001
  See application file for complete search history.

(56) References Cited

U.S. PATENT DOCUMENTS

| | | | |
|---|---|---|---|
| 5,923,421 A | 7/1999 | Rajic et al. |
| 6,192,351 B1 | 2/2001 | Persaud |
| 6,411,905 B1 | 6/2002 | Guoliang et al. |
| 6,422,061 B1 | 7/2002 | Sunshine et al. |
| 8,052,935 B2 | 11/2011 | Leininger et al. |
| 8,366,630 B2 | 2/2013 | Haick et al. |
| 9,678,059 B2 | 6/2017 | Haick et al. |
| 9,709,561 B2 | 7/2017 | Na et al. |
| 10,011,481 B2 | 7/2018 | Haick |
| D892,653 S | 8/2020 | Eason et al. |
| 2002/0092340 A1 | 7/2002 | Prater et al. |

(Continued)

FOREIGN PATENT DOCUMENTS

EP    0 922 212    6/1999

OTHER PUBLICATIONS

A.D. Wilson, Diverse Applications of Electronic-Nose Technologies in Agriculture and Forestry, 13 Sensors 2295-2348 (2013).

(Continued)

*Primary Examiner* — Jamil Ahmed
(74) *Attorney, Agent, or Firm* — FOLEY & LARDNER LLP

(57) ABSTRACT

Disclosed herein are devices and related methods for identifying odorants using a combination of light sources which enable discrimination between different odorants and/or determination of odorant concentration. The response of a chemical sensor to one or more odorants is observed under a combination and/or sequence of light sources, and the resulting data is subsequently analyzed using machine learning methods to identify one or more odorants and/or to determine the concentration of one or more odorants.

20 Claims, 19 Drawing Sheets

(56) References Cited

U.S. PATENT DOCUMENTS

| | | | |
|---|---|---|---|
| 2004/0135684 A1* | 7/2004 | Steinthal | G01N 33/0034 340/522 |
| 2006/0073483 A1* | 4/2006 | White | C12Q 1/6825 435/6.1 |
| 2008/0138911 A1 | 6/2008 | Robins | |
| 2012/0021932 A1* | 1/2012 | Mershin | G01N 33/0031 422/69 |
| 2014/0367579 A1* | 12/2014 | Otsuka | G01N 21/65 250/492.1 |
| 2020/0256840 A1 | 8/2020 | Doshi et al. | |

OTHER PUBLICATIONS

B.N. Johnson & R. Mutharasan, Biosensing Using Dynamic-Mode Cantilever Sensors: A Review, 32 Biosensors & Bioelec. 1 (2012).

D. Karakaya et al., Electronic Nose and Its Applications: A Survey, 17 Int'l J. Automation & Computing 179-209 (2020).

D.M. Karabacak et al., An Experimental Study Using Nanomechanical Resonators, 98 Phys. Rev. Lett. 254505 (2007).

Druett, Ovulation: What Is It, and How Do I Know When I'm Ovulating?, Clue (Nov. 22, 2017), https://helloclue.com/articles/cycle-a-z/ovulation-101-what-is-it-how-does-it-work.

https://shop.boselec.com/products/hsl-5-115.

https://www.mouser.ca/datasheet/2/256/maximintegratedproducts_MAX30102%20DS-1179649.pdf.

https://www.mouser.ca/datasheet/2/423/VAOL-5GUV8T4-1064834.pdf.

https://www.mouser.ca/datasheet/2/783/BST_BME680_DS001-1509608.pdf.

K. Jensen et al., An Atomic-Resolution Nanomechanical Mass Sensor, 3 Nature Nanotech. 533 (2008).

M. Li et al., Bottom-Up Assembly of Large-Area Nanowire Resonator Arrays, 3 Nature Nanotech. 88 (2008).

M.M. Ali et al., Principles and recent advances in electronic nose for quality inspection of agricultural and food products, 99 Trends in Food Sci. & Tech. 1-10 (2020).

P. B. Bhandare et al, Electronic Nose: A Review; Research and Reviews: Journal of Engineering and Technology v.2 (4) (2013), https://www.rroij.com/open-access/electronic-nose-a-review.php?aid=34413.

R.B. Bhiladvala & Z.J. Wang, Effect of Fluids on the Q Factor and Resonance Frequency of Oscillating Micrometer and Nanometer Scale Beams, 69 Phys. Rev. E 036307 (2004).).

Sensigent eNOSE? Cyranose Sensor, https://www.sensigent.com/products/Cyranose%20320%20brochure.pdf.

Sensigent, Cyranose? 320 Portable Handheld Electronic Nose, https://www.sensigent.com/products/C320%20Datasheet.pdf.

X.L. Feng et al., Very High Frequency Silicon Nanowire Electromechanical Resonators, 7 Nano Lett. 1953 (2007).

International Search Report and Written Opinion on PCT Appl. Ser. No. PCT/US2021/058847 dated Feb. 7, 2022 (13 pages).

\* cited by examiner

Confusion Matrix
*70 Examples; 30 Tests*

| | Air | Methanol | Windex | Acetone | Isopropyl Alcohol | Ethanol | Mineral Spirits |
|---|---|---|---|---|---|---|---|
| Air | 30 | 0 | 0 | 0 | 0 | 0 | 0 |
| Methanol | 0 | 27 | 0 | 1 | 2 | 0 | 0 |
| Windex | 0 | 0 | 30 | 0 | 0 | 0 | 0 |
| Acetone | 1 | 0 | 2 | 27 | 0 | 0 | 0 |
| Isopropyl Alcohol | 0 | 0 | 0 | 0 | 30 | 0 | 0 |
| Ethanol | 0 | 0 | 0 | 0 | 1 | 28 | 1 |
| Mineral Spirits | 0 | 0 | 0 | 0 | 1 | 0 | 29 |

FIG. 6

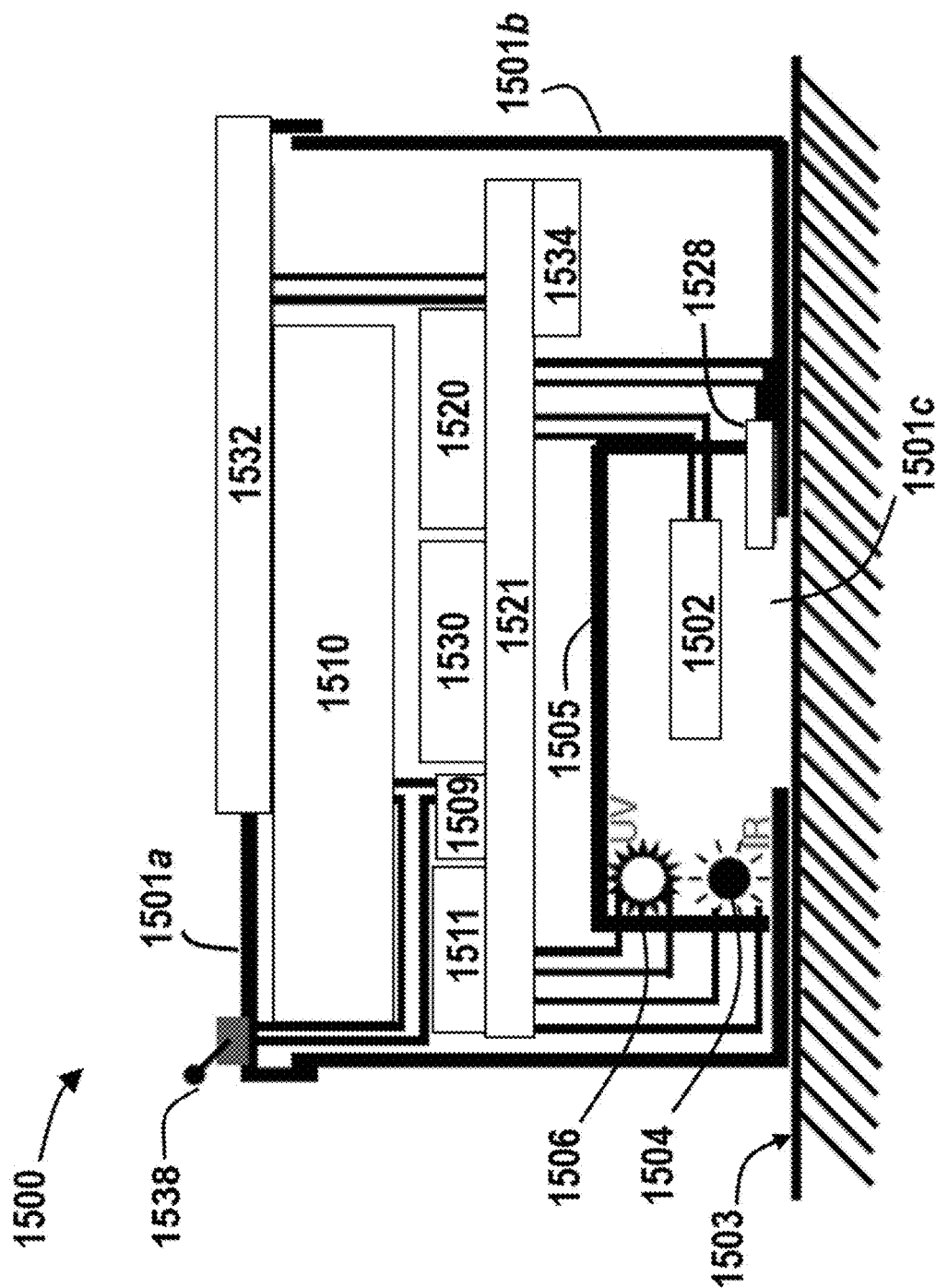

OLFACTORY SENSOR DEVICES AND RELATED METHODS

CROSS-REFERENCE TO RELATED APPLICATION

This application claims the benefit of and priority to U.S. Provisional Patent Application No. 63/112,394, filed on Nov. 11, 2020, the entire disclosure of which is incorporated by reference herein.

FIELD

The present disclosure relates generally to the field of odorant sensing devices. Disclosed herein are devices and related methods for identifying odorants using a combination of different light sources which enable discrimination between different odorants and/or determination of odorant concentration. The response of an odorant sensor to one or more odorants is observed under a combination and/or sequence of different light sources, and the resulting data is subsequently analyzed using, e.g., machine learning methods to identify and/or determine concentration of one or more odorants.

BACKGROUND

Real-time detection of odorants in air is an important problem for industrial production, air quality control, occupational health and safety, medicine, hospitality and travel, agriculture, law enforcement and public safety, mass transit, foods and beverages, cosmetics, and other fields. Existing odorant sensing devices deploy a large number of sensors in parallel. These sensors are based on, e.g., metal oxide semiconductors, mass-sensitive devices, bulk conducting polymers, polymer solvatochromic dyes, polymer composite sensors, and/or carbon-based semiconductors, which change resistance and/or capacitance upon exposure to particular odorants. (See. e.g., P. B. Bhandare et al., *Electronic Nose: A Review*, 2 RES. & REV.: J. ENG'G & TECH. (2013).) These devices simultaneously analyze the signals from multiple sensors, similar to the olfactory systems of animals.

The first practical implementation of this paradigm was demonstrated by AromaScan, Inc., which deployed a set of AromaScan electronic nose ("e-nose") sensors. These sensors are based on measuring electrical responses in arrays (24 or 32 units) of specially produced polymers sensitive to particular chemicals and subsequently analyzing the simultaneous signal using neural network methods such as fuzzy logic. (See, e.g., U.S. Pat. No. 6,192,351; EP 0922212A1.) Further studies have explored the possibility of measuring odorant concentrations using these devices. However, this method is indirect and is based on a nonlinear statistical regression, and determining the accuracy of this method is challenging. (See U.S. Pat. No. 6,411,905.) Despite their disadvantages and their relatively high cost, these devices find use in the food industry for quality control, among other applications. (See, e.g., M. M. Ali et al., *Principles and recent advances in electronic nose for quality inspection of agricultural and food products*, 99 TRENDS IN FOOD SCI. & TECH. 1-10 (2020); A. D. Wilson, *Diverse Applications of Electronic-Nose Technologies in Agriculture and Forestry*, 13 SENSORS 2295-2348 (2013)).

Currently, there are several manufacturers of devices based on existing e-nose technology. In conventional e-nose devices, successful discrimination among multiple odorants requires that the number of individual devices is correspondingly large. Additionally, these devices must collect and reference a large amount of data to discriminate a single odorant from among a large number of chemicals, which increases the difficulty, complexity, and cost of data acquisition and processing. For instance, the CYRANOSE® 320 Portable Handheld Electronic Nose currently available from Sensigent relies on 32 discrete polymer sensors. Gas sensors currently available from AerNos are based on MEMS technology specifically tuned to particular odorants, while multi-gas options are unavailable. Accordingly, the high cost and relative complexity of existing e-nose devices prevent widespread adoption of this technology in a broader range of practical applications.

Therefore, there exists a need for new sensing devices and sensing methods, which rely on new sensing paradigms to reduce the number of sensors required to discriminate among odorants—thereby reducing device size, cost, and complexity—while demonstrating high sensitivity and accurate odorant identification.

SUMMARY

Olfactory sensor devices according the present disclosure achieve the performance of an array of sensors while using a smaller number of sensors (e.g., a single sensor) by irradiating the sensor using one or more light sources influence the odorant adsorption-desorption kinetics of the sensor itself. The one or more light sources may be broadband light sources (e.g., infrared ("IR") and/or ultraviolet ("UV")). Olfactory sensor devices according the present disclosure do not rely on spectroscopic methods, which require scanning the detector electronics and/or narrow-band incident light through a range of wavelengths, then comparing acquired absorbance and/or transmission spectra to libraries of known spectra for a multitude of chemical species, all to identify a single odorant.

Instead, olfactory sensor devices according to the present disclosure use a single sensor (or a small number of sensors) which effectively performs similarly to a larger number of sensors due to the change of sensor properties when irradiated using one or more light sources (e.g., LR and/or UV irradiation).

In one aspect, the present disclosure relates to a method for identifying one or more odorants, comprising: exposing a sensor to one or more odorants to adsorb molecules of the one or more odorants onto the sensor surface; irradiating the sensor with a light sequence using one or more light sources to alter the adsorption kinetics of the molecules of the one or more odorants onto the sensor surface; measuring a change in one or more physical properties of the sensor during the irradiation; determining one or more characteristics of the one or more odorants based on the measured change during the irradiation. In some embodiments, the method further comprises inferring a property of a system from the one or more determined characteristics.

In some embodiments, determining the one or more characteristics of the one or more odorants comprises: maintaining, by the one or more processors, a machine learning model trained using a training data set comprising measured changes in one or more properties of the sensor in response to adsorption of one or more known odorants during the light sequence; and determining, by the one or more processors, the one or more characteristics by applying the measured change in one or more physical properties of the sensor during the irradiation to the machine learning model.

In some embodiments, the light sequence comprises a first irradiation comprising light having a first light characteristic and a second irradiation comprising light having a second light characteristic; and determining the one or more characteristics of the one or more odorants is based on a measured change of the one or more physical properties of the sensor during the first irradiation and a measured change of the one or more physical properties of the sensor during the second irradiation.

In some embodiments, the sensor comprises a resonator comprising a quartz crystal. In some embodiments, the sensor comprises nanowires comprising NiO, $TiO_2$, ZnO, $SnO_2$, $WO_3$, $In_2O_3$, $VO_2$, $V_2O_5$, $Al_2O_3$, or combinations thereof.

In some embodiments, the two or more light sources comprise an infrared light source and an ultraviolet light source. In some embodiments, the two or more light sources comprise at least one broadband light source.

In some embodiments, the light sequence comprises a first irradiation with a first light source for a first duration of time, a second irradiation with a second light source for a second duration of time, and a third irradiation with the first light source and the second light source for a third duration of time. In some embodiments, the light sequence is performed for more than one cycle.

In some embodiments, the one or more physical properties comprises a change in gain, a change in phase, or a change in impedance of the sensor. In some embodiments, the one or more physical properties is measured in comparison to a fixed resistor.

In some embodiments, the one or more characteristics of the one or more odorants comprises identity of the one or more odorants or concentration of the one or more odorants.

In some embodiments, the one or more odorants is contained within sweat vapor from a human subject.

In another aspect, the present disclosure relates to an olfactory sensor device, comprising: a sensor configured to adsorb odorant molecules; one or more light sources configured to irradiate the sensor during exposure of the sensor to odorant molecules; one or more processors communicably coupled to the sensor and the one or more light sources, wherein the one or more processors are configured to: operate the one or more light sources to produce a light sequence; measure a change in one or more physical properties of the sensor in response to adsorption of odorant molecules to the sensor during the light sequence; and identify one or more characteristics of the one or more odorant molecules by analyzing data associated with the measured change in one or more physical properties of the sensor.

In some embodiments, the sensor comprises a resonator comprising a quartz crystal. In some embodiments, the sensor comprises nanowires comprising NiO, $TiO_2$, ZnO, $SnO_2$, $WO_3$, $In_2O_3$, $VO_2$, $V_2O_5$, $Al_2O_3$, or combinations thereof.

In some embodiments, the one or more light sources comprises an IR light source or a UV light source. In some embodiments, the one or more light sources comprises a broadband light source.

In some embodiments, the olfactory sensor device comprises one or more auxiliary sensors in communication with the one or more processors. In some embodiments, the olfactory sensor device is wearable by a human subject.

BRIEF DESCRIPTION OF THE FIGURES

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

FIG. 6 is a confusion matrix for an embodiment of an olfactory sensor device according to the present disclosure, including a resonator crystal treated with NiO nanowires, in the presence of ambient air, methanol, ethanol, isopropanol, acetone, mineral spirits, and WINDEX®. The olfactory sensor device was trained with a training data set of seventy measurements for each odorant. The training data was then used to classify each odorant thirty times, with the number of correct classifications indicated in the black squares.

FIG. 15A is a schematic illustration (side perspective view) of an embodiment of a wearable olfactory sensor device according to the present disclosure.

DETAILED DESCRIPTION

Figure 1:
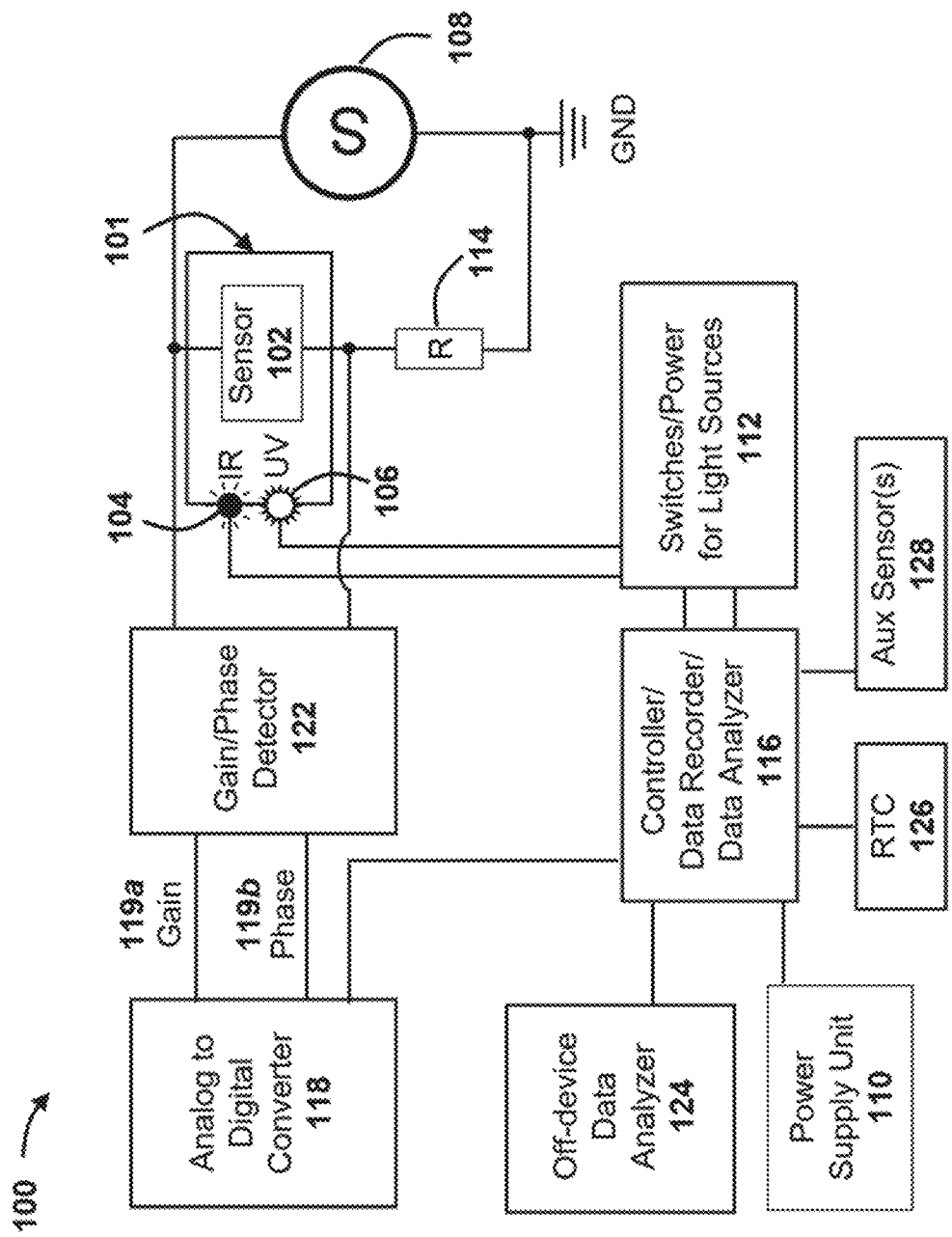
FIG. 1 is a schematic illustration of an embodiment of an olfactory sensor device according to the present disclosure.

Reference will now be made in detail to some specific embodiments contemplated by the present disclosure. While various embodiments are described herein, it will be understood that it is not intended to limit the present technology to the described embodiments. On the contrary, it is intended to cover alternatives, modifications, and equivalents as may be included within the spirit and scope of the technology as defined by the appended claims.

In the following description, numerous specific details are set forth in order to provide a thorough understanding of the present technology. Particular exemplary embodiments of the present technology may be implemented without some or all of these specific details. In other instances, well known process operations have not been described in detail in order not to unnecessarily obscure the present technologies.

Various techniques and mechanisms of the present technology will sometimes be described in singular form for clarity. However, it should be noted that some embodiments include multiple iterations of a technique or multiple instantiations of a mechanism unless noted otherwise.

Development of olfactory sensor (e-nose) devices over the past 20 years has focused on deploying a multitude of sensors in parallel, wherein responses from multiple sensors are analyzed to detect a chemical signature. (See, e.g., U.S. Pat. No. 6,192,351; EP 0922212A1; U.S. Pat. No. 6,411, 905; M. M. Ali et al., *Principles and recent advances in electronic nose for quality inspection of agricultural and food products*, 99 TRENDS IN FOOD SCI. & TECH. 1-10 (2020); D. Karakaya et al., *Electronic Nose and Its Applications: A Survey*, 17 INT'L J. AUTOMATION & COMPUTING 179-209 (2020); A. D. Wilson, *Diverse Applications of Electronic-Nose Technologies in Agriculture and Forestry*, 13 SENSORS 2295-2348 (2013).) In existing e-nose devices, every sensor produces a limited information set (e.g., adsorption rate of a particular chemical). (See US 2020/0256840; U.S. D892, 653S.) The information provided by a single sensor is insufficient for discriminating among large numbers of odorants, so multiple different sensors generating different types of information are required to discriminate between and among odorants. In some instances, this approach is employed for detecting small quantities of volatile odorants associated with the presence of human diseases. (See, e.g., U.S. Pat. Nos. 10,011,481; 9,678,059; 8,366,630; 8,052,932; 6,422,061.) In many cases, special fabrication and coating techniques are required to achieve sensitivities required for detecting volatile compounds (e.g., "VOCs") relevant to human health. Thus, previous designs for e-nose technology only work as combinations of large numbers of different devices with different odorant adsorption properties.

Unlike existing e-nose devices, olfactory sensor devices according to the present disclosure use the dynamic response of a single sensor to irradiation by different sequences of light sources or combinations of light sources (e.g., IR and/or UV sources). In some embodiments, the IR and/or UV sources comprise broadband light sources. For devices prepared according to the present disclosure, a single sensor is sufficient for detecting and discriminating among multiple odorants. In particular, the present disclosure describes exemplary embodiments in which a single sensor is capable of measuring odorant adsorption from the ambient air in real time, with periodic irradiation by a combination (e.g., a sequence) of IR and/or UV light. Devices thus prepared enable reliable discrimination between and among different odorants.

In particular, the present disclosure describes embodiments of olfactory sensor devices based on quartz resonators irradiated with infrared ("IR") and/or ultraviolet ("UV") light sources. Although the embodiments described herein use quartz resonators and combinations of broadband IR and/or UV light, these and other light source combinations will alter the odorant adsorption characteristics of chemically sensitive materials other than quartz resonators, such as sensors comprising polymers, polymer coatings, metal oxides, and other materials. Therefore, the principle of irradiating the sensor with a combination of different light sources (e.g., IR and/or UV light sources) applies broadly to devices utilizing sensors other than resonators as well. The present technology is thus capable of improving design and operation of olfactory sensor devices by making them substantially cheaper, less complex, and simpler to deploy, thereby enabling widespread use of olfactory sensor devices in a broad and diverse set of applications.

To illustrate olfactory sensor devices and related methods according to the present disclosure, herein are described olfactory sensor devices using mechanical resonators as sensors. Mechanical cantilevers/resonators and nano-resonator arrays have been successfully used for mass detection in the attogram range. (See, e.g., B. N. Johnson & R. Mutharasan, *Biosensing Using Dynamic-Mode Cantilever Sensors: A Review*, 32 BIOSENSORS & BIOELEC. 1 (2012); M. Li et al., *Bottom-Up Assembly of Large-Area Nanowire Resonator Arrays*, 3 NATURE NANOTECH. 88 (2008); K. Jensen et al., *An Atomic-Resolution Nanomechanical Mass Sensor*, 3 NATURE NANOTECH. 533 (2008).) Narrow band resonators (e.g., resonators with extremely high Q factors) permit detection of adsorption of extremely small quantities of matter on the resonators via the small (usually parts per million) frequency shift caused by adsorption. However, one disadvantage of these methods is that the high sensitivity requires maintaining the high Q-factor of the resonator, which in turn requires operating the resonator under high vacuum conditions, in the presence of very low quantities (e.g., very low concentrations) of adsorbate molecules. (See, e.g., X. L. Feng et al., *Very High Frequency Silicon Nanowire Electromechanical Resonators*, 7 NANO LETT. 1953 (2007); D. M. Karabacak et al., *An Experimental Study Using Nanomechanical Resonators*, 98 PHYS. REV. LETT. 254505 (2007); R. B. Bhiladvala & Z. J. Wang, *Effect of Fluids on the Q Factor and Resonance Frequency of Oscillating Micrometer and Nanometer Scale Beams*, 69 PHYS. REV. E 036307 (2004).) Moreover, since the principle of operation is purely mechanical, discriminating between different adsorbate chemicals is difficult. Thus, these mechanical resonator devices are difficult to deploy in practical applications.

Several improvements to classical resonator techniques have been suggested, such as increasing the sensitivity by creating porosity within the sensing zone, with the subsequent use of Raman spectroscopy for differentiation between chemicals captured by the device. (See U.S. Pat. No. 9,709, 561.) Alternatively, use of narrow-band infrared radiation of particular wavelength (e.g., monochromatic IR irradiation) has been suggested for selectivity. (See U.S. Pat. No. 5,923, 421.) Other constructs have used sensor materials that change their light absorption properties (e.g., absorption wavelengths) when target analytes are present in the air. (See US 2008/0138911 A1.) However, this approach still requires narrow-band light sources to analyze the absorption spectrum of the substrate.

The use of alternative light sources (e.g., incandescent sources, LEDs, lasers, and others) has been proposed for analyzing the physical behavior (e.g., amplitude and deflection) of the cantilever itself. However, such systems require high collimation of the light source and can realistically only use laser radiation. (See US 2002/0092340A1.) Moreover, the IR irradiation used in this approach measures the physical response of the cantilever and does not affect the properties of molecular adsorption and desorption from the cantilever. Further, the setup itself is complex (e.g., requiring at least two cantilevers) and is difficult to implement in field-ready experiments. In contrast, olfactory sensor devices according to the present disclosure do not require multiple sensors.

The use of Raman Spectroscopy or scanning through narrow wavelengths for sensor irradiation poses challenges for practical use of olfactory sensor technology. (See, e.g., U.S. Pat. Nos. 9,709,561; 5,923,421; US 2008/0138911A1.) Indeed, devices performing a narrow-band scans through IR spectra (e.g., monochromators) are expensive (thousands to tens of thousands of dollars), are too sensitive (unless well-protected under controlled environments), and are thus unsuitable for field deployment. Extremely narrow-band filters having a waveband for only one characteristic chemical peak (e.g., for ethanol) are costly, yet they are not sensitive enough to distinguish between chemically similar adsorbates (e.g., ethanol versus methanol). Cheaper light filters are available, but they have a broader transmission band and are not able to discriminate between chemicals with similar spectral peaks.

On the other hand, olfactory sensor devices according to the present disclosure circumvent the drawbacks of the above-discussed devices by using single sensors that change their odorant adsorption properties in response to irradiation under different broadband light sources that are relatively cheap, robust, simple, and easy to deploy in the field. Moreover, olfactory sensor devices prepared according to the present disclosure do not rely on spectral identification of odorants and instead use the change in observed physical properties of the sensor to identify and distinguish among different odorants.

To guide the description of olfactory sensor devices according to the present disclosure, reference is made, by way of non-limiting example, to particular embodiments of the present technology. Referring to FIG. 1, one embodiment an olfactory sensor device 100 is assembled using a 4 MHz quartz crystal resonator (Mouser Electronics, #815-AB308-4.000) as a sensor 102 (see also FIG. 2). The resonator was coated with a layer of NiO nanowires by drop-casting from aqueous solution, then drying in ambient atmosphere.

Referring still to FIG. 1, the sensor 102 (e.g., resonator crystal with electrical leads) is positioned inside a container or outer shell 101 equipped with broadband infrared 104 and broadband ultraviolet LED 106 light sources (Mouser Electronics, #593-VAOL5GUV8T4 and/or #593-VAOL5EUVOT4) configured to irradiate the sensor 102 while the sensor 102 is exposed to one or more odorant molecules. The sensor (e.g., resonator) 102 is driven at a single frequency using a function generator (e.g., frequency generator) 108. The light sources are communicably coupled to a controller 116 and relays 112 configured to turn on and off the UV and IR light sources in a particular light sequence. In this embodiment, for example, the controller 116 and relays 112 may cycle the light sources 104, 106 through any number of combinations of light. For instance, this embodiment may cycle the light sources in the following light sequence: (1) no light (25 sec); (2) IR only (25 sec); (3) IR+UV (25 sec); and (4) UV only (25 sec). One of ordinary skill will recognize that other light sequences are possible. The light sequence may be repeated for a number of cycles.

Referring still to FIG. 1, adsorption of one or more odorants by the sensor 102 is monitored by measuring changes one or more physical properties of the sensor during irradiation by the one or more light sources. For example, in some embodiments, the one or more physical properties includes the sensor's amplitude, gain, and/or phase in response to a single frequency. To facilitate measuring changes in the one or more physical properties, the sensor 102 is connected to a resistor 114 in series, and the voltage from the resistor and sensor are measured by a gain and phase detector 122 communicably coupled to the controller/data recorder 116. The gain/phase detector 122 is communicably coupled to a 16-bit analog-to-digital converter (ADC) circuit and communicates the gain 119a and phase 119b signals from the sensor 102 to the ADC 118. The response of the sensor 102 to a single frequency, with respect to a resistor 114, is recorded by the controller/data recorder (e.g., a logic board having a processor) 116 through the ADC 118, and then transmitted to a data analyzer 116, 124 for analysis. In this embodiment, the data analyzer comprises a ELEGOO Nano Board CH340/ATmega328P processor. In some embodiments, the data analyzer 116, 124 may be located on the device or off the device.

In some embodiments, the olfactory sensor device further comprises a real-time clock (RTC) 126 communicably coupled to the controller/data recorder 116. Further, the olfactory sensor device further comprises a power supply unit 110 communicably coupled to the controller/data analyzer 116 and any of the other components discussed above for the purpose of powering their operation. The power supply unit may comprise any suitable component for supplying electrical power to the various electrical components of the olfactory sensor device. In some embodiments, the power supply unit 110 is a battery (e.g., a Li-poly battery), though one of ordinary skill in the art will recognize that other suitable power supply units are within the scope and spirit of the present disclosure.

The data analyzed by the data analyzer 116, 124 may be output to a display device. In some embodiments, the display device is built into the olfactory sensor device and is in communication with the data analyzer 116, 124. In some embodiments, the display device is an external display in communication with the data analyzer 116, 124. In some embodiments, the data analyzed by the data analyzer may be shown on a display device in real time.

Sensors

Figure 2:
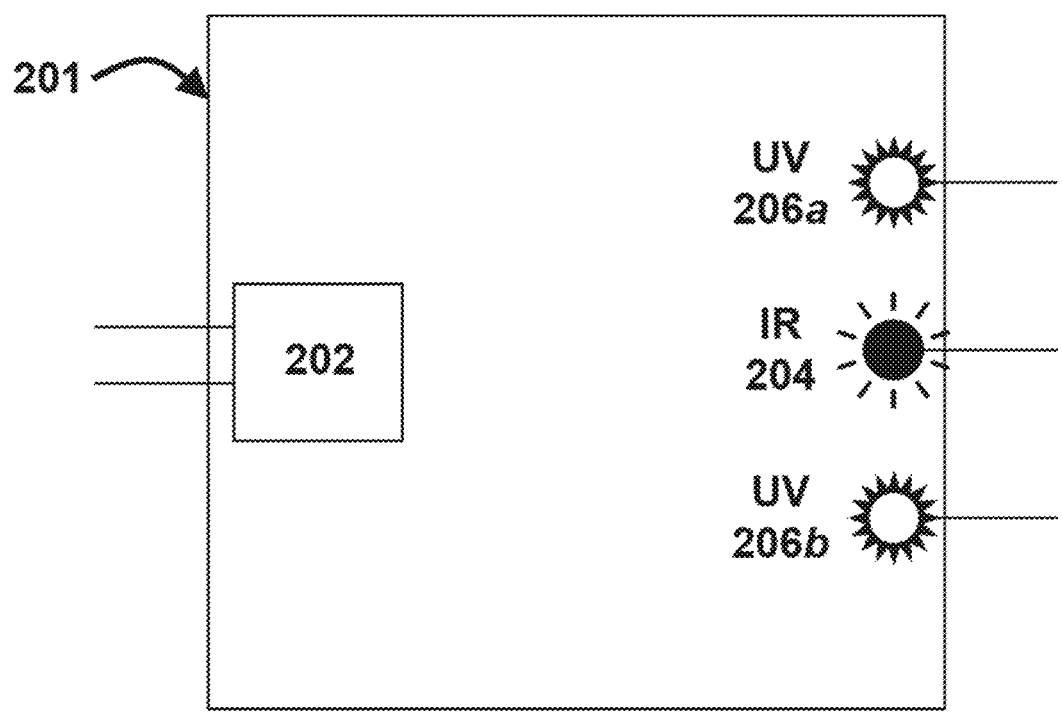
FIG. 2 is schematic illustration of an embodiment of a sensor chamber for an olfactory sensor device according to the present disclosure, comprising a sensor and multiple light sources.

Referring to FIGS. 1 and 2, olfactory sensor devices 100 according to the present disclosure comprise one or more sensors 102, 202. In some embodiments, the sensor is placed inside a container or outer shell 101, 201 equipped with one or more light sources 104, 204, 106, 206a, 206b. Odorant molecules adsorb to a sensor surface from the surrounding environment (e.g., ambient air) to alter one or more physical properties of the sensor.

The sensor may comprise any suitable material for adsorbing odorant molecules and for facilitating measurement of one or more physical properties of the sensor. In some embodiments, the sensor comprises one or more metals (e.g., gold, silver, platinum, copper, aluminum, nickel, aluminum, etc.), insulators (e.g., glasses, quartz, non-conducting oxides, etc.), semiconductors (e.g., Si, GaAs, etc.), conductive oxides (e.g., indium tin oxide), polymers (e.g., poly(ethylene oxide), poly(styrene), poly(vinyl acetate), poly(vinyl butyral), other conductive thermoset polymers, or other conductive thermoplastic polymers) or conductive polymer nanocomposites (e.g., such as carbon nanotube ("CNT")-reinforced poly(caprolactone) ("PCL"), CNT-poly(lactic acid) ("PLA"), CNT-poly(carbonate) ("PC"), CNT-poly(methyl methacrylate) ("PMMA"), CNT-biobased polyester ("BPR"), etc.), or combinations thereof.

In some embodiments, the sensor comprises a resonator (e.g., a quartz crystal resonator). In some embodiments, the sensor comprises a 4 MHz quartz crystal resonator which has a narrow resonance and high sensitivity. Quartz crystal resonators are readily available in bulk quantities, compact, easily-handled, and relatively inexpensive. However, one of ordinary skill in the art will recognize that other components may also be used as the one or more sensors and are within the scope of this disclosure. Further, multiple sensors and multiple types of sensors may be used in a single olfactory sensor device.

Sensor Surface Modification

Further, in some embodiments, the sensor surface may be modified with a surface layer to enhance the surface area available for adsorption of odorant molecules or to enhance the sensitivity of the sensor surface to irradiation by incident light from light sources (e.g., IR and/or UV light), which in turn alters the kinetics of odorant molecule adsorption to or desorption from the sensor. In some embodiments, the sensor surface is modified using a surface layer of nanoparticles (e.g., nanowires, nanospheres, nanoprisms, nanorods, nanofibers, nanotubes, or combinations thereof), polymer films, metallic films, oxide films, self-assembled monolayers, carbon-based materials (e.g., carbon nanotubes, graphene, etc.), two-dimensional electronic materials (e.g., boron nitride, transition metal dichalogenides such as MoS2, etc.), or any other suitable material for enhancing the surface area of the sensor or enhancing the sensor sensitivity to irradiation by incident light. In some embodiments, the sensor surface is modified using a surface layer of nanowires. In some embodiments, the nanowires comprise NiO, $TiO_2$, ZnO, $SnO_2$, $WO_3$, $In_2O_3$, $VO_2$, $V_2O_5$, $Al_2O_3$, or combinations thereof.

The sensor surface may be modified by using any suitable method for depositing a surface layer onto the sensor. For example, in some embodiments, the surface layer may be deposited onto the sensor by drop-casting, lithographic methods, chemical vapor deposition, physical vapor deposition, electrodeposition, direct growth of nanostructures on the sensor surface (e.g., vapor-liquid-solid growth), or any other suitable method. In some embodiments, the sensor surface is modified by drop-casting a surface layer (e.g., NiO nanowires) from solution onto the sensor surface, followed by a drying step (e.g., heat drying).

Multiple Sensors

In some embodiments, olfactory sensor devices according to the present disclosure comprise multiple sensors in parallel, to enhance sensitivity or to discriminate between larger numbers of odorants. Thus, in some embodiments, olfactory sensor devices according to the present disclosure comprise more than one sensor. In some embodiments, the number of sensors may be at least 1, at least 2, at least 3, at least 4, at least 5, at least 6, at least 7, at least 8, at least 9, at least 10, at least 20, at least 30, at least 40, at least 50, at least 100, at least 200, at least 300, at least 400, at least 500, at least 1,000, or more, in parallel. In embodiments comprising more than one sensor, each individual sensor may be identical to the other sensor(s) or different from the other sensor(s) in terms of material choice, size, surface modification, physical properties, or any other characteristic that may facilitate enhanced discrimination between and among different odorants. In some embodiments, the number of sensors is two or greater, the two or more sensors are each resonators, and the two or greater sensors operate at the same resonant frequency.

Auxiliary Sensors

Referring still to FIG. 1, optionally, the data collected using the sensor may be augmented and/or supplemented by data collected using one or more auxiliary sensors 128 (e.g., pressure sensors, temperature sensors, humidity sensors, accelerometers, or VOC sensors). A non-limiting example of such sensors is a BME680 sensor currently offered by Bosch. In particular, for wearable devices, in addition to the types of sensors discussed above, data collected by the sensor may be augmented and/or supplemented by data collected using, e.g., a heart rate/$O_2$ saturation sensor. A non-limiting example of such sensors is a Maxim Integrated MAX30102 sensor currently available from Maxim Integrated. One of ordinary skill in the art will recognize that other such sensors are within the scope of this disclosure. Such auxiliary sensors 128 are optional and may be used concurrently with the olfactory sensor device described herein to provide data (e.g., heart rate, oxygen saturation, humidity, etc.) in addition to one or more characteristics of one or more odorants.

Light Sources

In existing e-nose devices, the sensors are usually manufactured from polymers that undergo a change in impedance upon adsorption of odorant molecules from the surrounding environment. However, once the individual sensors are fabricated, their properties cannot be changed and need to be operated as fabricated for the entire life cycle of the device. In contrast, olfactory sensor devices according to the present disclosure, even if having only one sensor, can operate as a sensor array by taking advantage of changes in kinetics of odorant molecule adsorption by sensor surfaces during exposure to different light sources (e.g., IR and/or UV light).

Referring again to FIGS. 1 and 2, olfactory sensor devices according to the present disclosure include one or more light sources (104, 106, 204, 206a, 206b) for generating any suitable type of incident light to alter the kinetics of odorant molecule adsorption-desorption to the sensor surface. In some embodiments, the incident light may be, for example, infrared light, visible light, ultraviolet light, microwave irradiation, radio frequency irradiation, or any combination thereof.

In some embodiments, the one or more light sources are broadband light sources, as characterized by having a half-width at half-maximum (HWHM) of at least 1 nm, at least 2 nm, at least 3 nm, at least 4 nm, at least 5 nm, at least 10 nm, at least 20 nm, at least 25 nm, at least 30 nm, at least 40 nm, at least 50 nm, at least 60 nm, at least 70 nm, at least 80 nm, at least 90 nm, at least 100 nm, at least 200 nm, at least 300 nm, at least 400 nm, at least 500 nm, at least 600 nm, at least 700 nm, at least 800 nm, at least 900 nm, at least 1 µm, at least 2 µm, at least 3 µm, at least 4 µm, at least 5 µm, at least 6 µm, at least 7 µm, at least 8 µm, at least 9 µm, at least 10 µm, at least 20 µm, at least 30 µm, at least 40 µm, at least 50 µm, at least 60 µm, at least 70 µm, at least 80 µm, at least 90 µm, or at least 100 µm.

In some embodiments, an olfactory sensor device according to the present disclosure comprises one or more IR light sources (e.g., a HSL-5-115 infrared lamp currently available from Boston Electronics) having a HWHM of 1-20 µm, 2-15 µm, or 3-10 µm. In some embodiments, an olfactory sensor device according to the present disclosure comprises one or more UV light sources (e.g., a VAOL-5GUV8T4 UV LED lamp currently offered by Visual Communications Company) having a HWHM of 10 nm-1 µm, 10-500 nm, 10-250 nm, 10-100 nm, 10-80 nm, 10-60 nm, 10-50 nm, 10-40 nm, or 10-30 nm. For purposes of this disclosure, the term "broadband" refers to light sources with HWHM values within these ranges or broader ranges. Such light sources would not be useful for spectrometry. However, using such readily-available broadband light sources allows the user to effectively modify the odorant molecule adsorption properties by using a combination of light sources. The broadband light produced by an incandescent IR light source and/or by UV diodes, for example, is of great interest because such light sources are reliable, consume relatively little power, are easily obtained, and are readily deployed.

In some embodiments, olfactory sensor devices according to the present disclosure comprise combinations of one or more light sources which irradiate the sensor to change the effective adsorption properties of the sensor toward different odorants. For example, in some embodiments, the combination of light sources comprises IR light, UV light, IR+UV light, and no light (darkness). Thus, a single sensor, irradiated by a sequence of N different light combinations, will provide information equivalent to an array of N different sensors. The measurement of the dynamic response of the sensor to the individual light combinations allows the user to deploy a single sensor that is capable of identifying and/or discriminating among different odorants without any need for monochromatic irradiation or implementing a multitude of sensors.

Additionally, the one or more light sources allows a single sensor to operate as multiple sensors with tunable parameters. In some embodiments, this can be achieved by increasing or decreasing the current through the one or more light sources (e.g., an incandescent IR source), or by operating multiple diodes (e.g., UV diodes) at once. Unlike the traditional design of e-nose sensors, the effective modification of sensor properties by incident broadband IR and/or UV light can be undertaken dynamically, for example, by adjusting the incident light properties (e.g., intensity, flux, etc.) to the odorant concentration to enhance sensitivity, or by increasing or decreasing the number of light combinations to enhance recognition of multiple odorants.

In some embodiments, olfactory sensor devices according the present disclosure may comprise several light sources, or a single modulated light source. For instance, in some embodiments, the intensity of a light source may be modulated, or multiple broadband diodes with different central wavelengths or HWHM could be used, alone or in combination. In principle, the number of light source combinations is unlimited. Additionally, the number of light sources is in principle unlimited and may be 1 or more, 2 or more, 3 or more, 4 or more, 5 or more, 10 or more, 20 or more, 30 or more, 40 or more, 50 or more, 100 or more, or any range or value therein between.

The intensity of incident light on the sensor will also affect the odorant adsorption kinetics onto the sensor. For different light intensities from the same light source, different sensor responses are expected. Thus, to further expand the number of light source combinations available, the one or more light sources may also change their position(s) relative to the sensor (e.g., distance from the sensor) and/or orientation relative to the sensor to control the intensity of radiation on the sensor. The one or more light sources may also change their intensity by adjusting the power supplied to the one or more light sources to provide a different response (e.g., different intensity of radiation on the sensor). In this way, a single light source may act as multiple different light sources by altering its position relative to the sensor, orientation relative to the sensor, or output intensity. In some embodiments, the device may contain 2 or more sources of UV light and/or and IR light, having the same or different power and spectral emission properties. Multiple, similar light sources may be used simultaneously to increase the intensity of incident light on the sensor. For instance, two or more identical UV light sources may be used at the same time to multiply the intensity of incident light on the sensor.

In some embodiments, irradiating the sensor with a light sequence using one or more light sources will alter the adsorption (or adsorption-desorption) kinetics of molecules of one or more odorants onto the sensor surface. In some embodiments, the light sequence comprises a first irradiation comprising light having a first light characteristic. In some embodiments, the light sequence further comprises a second irradiation comprising light having a second light characteristic. In some embodiments, the first and second irradiations use the same light source (e.g., a single light source). In some embodiments, a light characteristic may comprise one or more of type of light (e.g., UV, IR, etc.), bandwidth (FWHM, HWHM), intensity, wavelength (e.g., median wavelength, average wavelength, maximum wavelength, minimum wavelength, or combinations thereof), wavelength range, frequency, frequency range, or duration of irradiation (seconds). In some embodiments, the first light characteristic and the second light characteristic are the same. In some embodiments, the first light characteristic and the second light characteristic are different.

In some embodiments, olfactory sensor devices according to the present disclosure, may use any combination of light sources, alone or in combination, in any sequence, for any amount of time, to further enhance sensitivity and the ability to discriminate among large numbers of odorants. In some embodiments, olfactory sensor devices use a light sequence comprising, e.g., UV light, IR light, UV+IR light, and/or no light, for any duration, in any order, for any number of cycles. In some embodiments, olfactory sensor devices according the present disclosure use a light sequence comprising: (1) no light (25 seconds); (2) IR light (25 seconds); (3) UV light (25 seconds): and (4) IR+UV light (25 seconds). In some embodiments, the light sequence is repeated for n cycles, where n is 1, 2, 3, 4, 5, 10, 20, 30, 40 50, 100, 200, 300, 400, 500, 1000, 2000, 3000, 4000, 5000, or 10,000, or more, or any range or value therein. In some embodiments, one or more characteristics of one or more odorants are determined by irradiating the sensor using a light sequence performed for only one cycle or less.

Physical Property Measurement

In some embodiments of olfactory sensor devices and related methods according to the present disclosure, changes in physical properties of the sensor are measured during exposure of the sensor to odorant molecules. Measuring the changes in the physical properties of the sensor during adsorption of odorant molecules to the sensor surface permits determination of the amount of odorant adsorbed over time (e.g., during irradiation of the sensor with a particular light source or combination of light sources) and determination of kinetics of odorant adsorption which are unique to a particular odorant under particular conditions (e.g., irradiation conditions), thereby enabling the identification of one or more odorants.

The measured physical properties may be any properties suitable for observing odorant adsorption to the sensor and may include change in gain, change in phase, change in resonant frequency, change in resistivity, change in impedance, change in amplitude, etc. In some embodiments, the changes in physical properties of the sensor comprise the change in gain or change in phase of the sensor. In some embodiments, the changes in physical properties of the sensor comprise the change in gain or change in phase of the sensor measured relative to a fixed component (e.g., resistor or capacitor). In some embodiments, the changes in physical properties of the sensor comprise a combined measure of change in gain and change in phase, or any other combination of one or more measured properties.

In some embodiments, olfactory sensor devices according to the present disclosure comprise one or more processors communicably coupled to the sensor and one or more (e.g., two or more) light sources, wherein the one or more processors are configured to: operate the one or more (e.g., two or more) light sources to produce a light sequence; measure a change in one or more physical properties of the sensor in response to adsorption of odorant molecules to the sensor during the light sequence; and identify one or more characteristics of one or more odorant molecules by analyzing data associated with the measured change in one or more physical properties of the sensor.

In some embodiments, the one or more processors may comprise an "on-board" processor (or microcontroller comprising a processor), such as a Raspberry Pi processor, ATmega328 microcontroller (or Arduino Nano), or an equivalent processor, such as an ELEGOO Nano Board CH340/ATmega328P microcontroller. In some embodiments, the processor or microcontroller is an Adafruit ItsyBitsy nRF52840 Express—Bluetooth LE microcontroller board in combination with a nRF52840 ARM Cortex M4 processor. In some embodiments, some or all of the data processing or data analysis may be carried out "off-device," or remotely, such as by using a bluetooth device in combination with a smart phone application or by using a cloud-based processing system.

When exposed to one or more odorants, odorant molecules will attach and detach to the sensor surface until an equilibrium condition is reached. During a measurement, each sensor is vibrated at a frequency close to its resonance frequency, but its oscillation amplitude and phase will change considerably as molecules attach and detach from the sensor surface, leading to a measurable change in impedance, until a new equilibrium condition is reached. The impedance of the sensor (e.g., crystal resonator), connected in series by a fixed resistor to ground, is measured using a gain and phase detector by comparing the ratio of amplitudes (gain) and the difference in phase of two sinusoidal electric signals. One signal is taken as the applied signal at the crystal and resistor system, and another one at the crystal-resistor juncture.

In some embodiments, the light sources are cycled through a light sequence (e.g., no light (25 sec), IR only (25 sec), IR+UV (25 sec), UV only (25 sec)). At the beginning of each change in light conditions, the molecular adsorption-desorption kinetics of the sensor-odorant system change compared to those obtained under the preceding light conditions. Thus, at each change in light conditions, the sensor-odorant system is no longer at attachment-detachment equilibrium.

Accordingly, from the moment of the light condition change, the attached mass on the crystal varies, causing a measurable change in the impedance of the sensor. The change of the impedance over several seconds is analyzed by one or more processors and recorded as data, before the next change in light conditions. Under each light condition, several hundred data points are recorded, which are then analyzed using curve-fitting procedures. The parameters of curve fits to the data for each light condition ($A_0$, $A_1$, $A_2$, etc.) form the output of the sensor and are used as an input to machine learning algorithms to either "train" the olfactory sensor device or to classify one or more odorants.

Machine Learning

Olfactory sensor devices according to the present disclosure operate based on measuring changes in one or more physical properties of one or more sensors caused by changes in the adsorption and desorption of odorant molecules on the sensor surface during irradiation using a light sequence using one or more light sources. In particular, the independent and possibly simultaneous operation of different light sources (e.g., broadband infrared (IR) and ultraviolet (UV) light) causes measurable changes in physical properties of the sensor unique to each odorant.

In contrast to existing "e-nose" devices, olfactory sensor devices according the present disclosure do not discriminate between different odorants by directly identifying different odorants through their infrared spectra. Instead, the olfactory sensor device according to the present disclosure discriminates between different odorants by the chemical-dependent response of the device. Odorant identification or discrimination is provided not by reference to known IR and UV spectral tables, but by a learned response of the device and the use of data analytics to discriminate between odorants that the olfactory sensor device has been "trained" to recognize. The olfactory sensor device according to the present disclosure thus draws inspiration from the human or animal nose, which does not rely on the presence of particular peaks in a spectrum, but the learned response of specially coded cilia to odorants.

In some embodiments of olfactory sensor devices and related methods according to the present disclosure, determining one or more characteristics of the one or more odorants (e.g., unknown odorant(s)) is accomplished by inferring the one or more characteristics from the measured change in the one or more physical properties of the sensor based on a machine learning model which has been "trained" using measured changes of physical properties for known odorants. In some embodiments, the determining is performed using a machine learning algorithm. In some embodiments, the one or more characteristics may comprise odorant identity, concentration, two-dimensional or three-dimensional configuration (e.g., secondary, tertiary, or quaternary arrangement of biomolecules such as proteins), optical isomerism, polarity, or any other suitable characteristic of interest.

Figure 3:
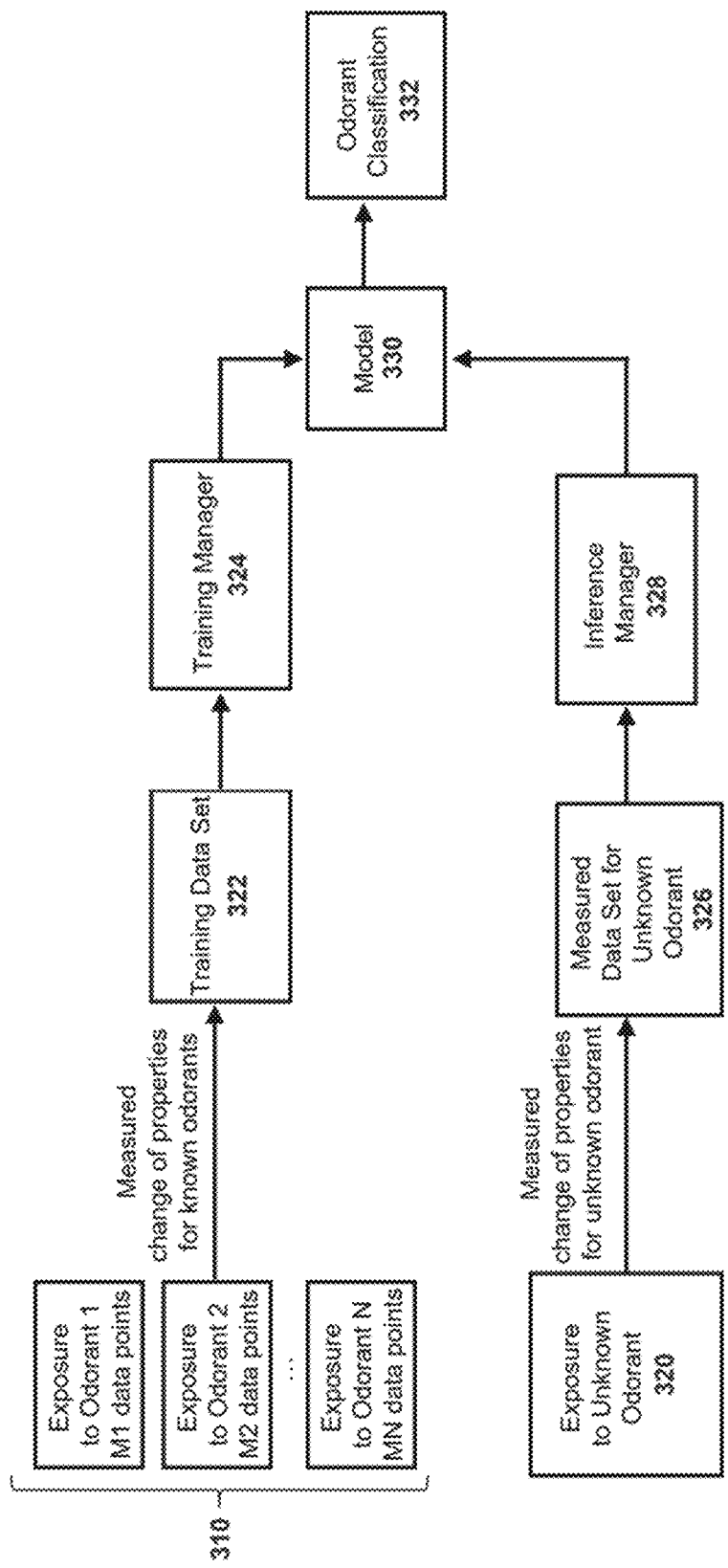
FIG. 3 is a block diagram of a machine learning process for an embodiment of an olfactory sensor device according to the present disclosure.

Referring now to FIG. 3, in some embodiments, the determining is performed by maintaining a machine learning model 330. In some embodiments, the machine learning model includes a training manager 324 and an inference manager 328. The training manager 324 may train the model 330 based on a training data set 322. The training data set 322 includes measurement data associated with the change in one or more physical properties of the sensor in the presence of known odorants, while the sensor is irradiated with one or more different light sequences. The training data set 322 includes the measured change of one or more properties of the sensor upon exposure to one or more (e.g., 1, 2, 3, . . . , N) odorants while the sensor is irradiated with one or more different light sequences. The training manager 324 can perform various training algorithms to train the model 330 to determine one or more characteristics of one or more odorants based on an inference data set 326. The model 330 can be any form of artificial intelligence and/or machine learning.

Referring still to FIG. 3, in one embodiment, the algorithm uses the parameters obtained 310 from exposure of the sensor to one or more known odorants during irradiation using a known light sequence as an input of the training model 330. For classification (identification) of odorants, an assembly of data from one or more known odorants is used as a training data set 322. Each odorant is characterized by one or more parameters under each known light condition, giving a total number of parameters for each odorant equal to the number of parameters multiplied by the number of light conditions. The parameters are recorded in a training data set 322 and used to train a machine learning algorithm, which may be any suitable machine learning algorithm. Representative examples include Logistic Regression, Linear Discriminant Analysis, K-Neighbors Classifier, Decision Tree Classifier, Support Vector Machines or other classification algorithms. One of ordinary skill in the art will recognize that other algorithms are within the spirit and scope of this disclosure.

The algorithm then uses the input data for measured change in properties of the sensor exposed to an unknown odorant 320 under a known light sequence. The measured data set 326 is compared to the training data set 322, which contains data from one or more learned odorants, and the model 330 produces the "best guess" regarding the unknown odorant from among the odorants "learned" by the model in the training data set 322.

In some embodiments, the inference manager 328 is configured to apply the inference data set 326 (e.g., measured changes in one or more physical properties of a sensor exposed to one or more unknown odorants under one or more known light conditions), to the model 330. The output may be one or more characteristics of one or more odorants 332.

In some embodiments, olfactory sensor devices according to the present disclosure are capable of detecting and identifying an odorant in real time. In some embodiments, olfactory sensor devices according to the disclosure detect and identify one or more odorants within one cycle (e.g., one light sequence) or within a small number of cycles (e.g., few light sequences).

In some embodiments, an olfactory sensor device according to the present disclosure may be capable of identifying an odorant in less than or equal to 1 cycle, less than or equal to 2 cycles, less than or equal to 3 cycles, less than or equal to 4 cycles, less than or equal to 5 cycles, less than or equal to 6 cycles, less than or equal to 7 cycles, less than or equal to 8 cycles, less than or equal to 9 cycles, less than or equal to 10 cycles, less than or equal to 20 cycles, less than or equal to 30 cycles, less than or equal to 40 cycles, less than or equal to 50 cycles, less than or equal to 60 cycles, less than or equal to 70 cycles, less than or equal to 80 cycles, less than or equal to 90 cycles, less than or equal to 100 cycles, less than or equal to 150 cycles, less than or equal to 200 cycles, less than or equal to 250 cycles, less than or equal to 300 cycles, less than or equal to 350 cycles, less than or equal to 400 cycles, less than or equal to 450 cycles, less than or equal to 500 cycles, less than or equal to 600 cycles, less than or equal to 700 cycles, less than or equal to 800 cycles, less than or equal to 900 cycles, less than or equal to 1,000 cycles, less than or equal to 10,000 cycles, or less than or equal to 100,000 cycles, or any range or value therein.

Inferring Properties of Systems

In some embodiments, the one or more determined characteristics of the one or more odorants may be used to infer a property of a system. Non-limiting examples of systems include the body of a subject (e.g., a human or animal), one or more sub-systems of the body of a subject (e.g., blood, circulatory system, digestive system, endocrine system, nervous system, etc.), a health care facility (e.g., a doctor's office, emergency room, hospital room, etc.); care facilities (elder care, infant care, or child care facility), a worksite (e.g., industrial site, mine, mineshaft, laboratory, etc.), agricultural site (e.g., food storage, livestock housing), hotel room, restroom, etc. In some embodiments, the inferred property may indicate a condition of the system. For example, the inferred property may be blood glucose levels, ovulation status, onset of long-term illness occurrence of an acute health event such as a heart attack, stroke, or broken bone, a toxic substance leak or spill (e.g., in a laboratory or industrial site), toxic gas concentration (e.g., $H_2S$ in a mine), the degradation or spoilage of stored food, the certification status of food (e.g., "organic"), or the overall health of a livestock population (e.g., in a chicken coop), among others. One of ordinary skill in the art will recognize that other inferred properties and systems are within the scope and spirit of the present disclosure.

In these embodiments, one or more olfactory sensor devices may be in communication with a notification system (e.g., an alarm, a display, a paging system, a cloud-based data collection system) configured to track inferred properties of a system (e.g., if one or more odorants indicating a public health threat) when one or more characteristics of one or more odorants is determined, and a property of a system is inferred. Thus, when one or more olfactory sensor devices infers a property of a system, one or more olfactory sensor devices communicate a message (e.g., alarm, text message, phone call, message on a remote display, etc.) to cloud-based tracking system or to the appropriate professionals or officials, who may be on-site or off-site, to facilitate early detection, intervention, or coordination of a response.

EXAMPLES

Olfactory sensor devices according to the present disclosure will now be described with respect to particular exemplary embodiments, which are not intended to limit the scope of the present disclosure. For all examples discussed below, olfactory sensor devices were constructed as described above in the Detailed Description, though persons of ordinary skill in the art will understand that other device constructions are possible and would not depart from the scope and spirit of this disclosure.

Example 1. Data Processing—Clean Crystal Reference Data

Figure 4:
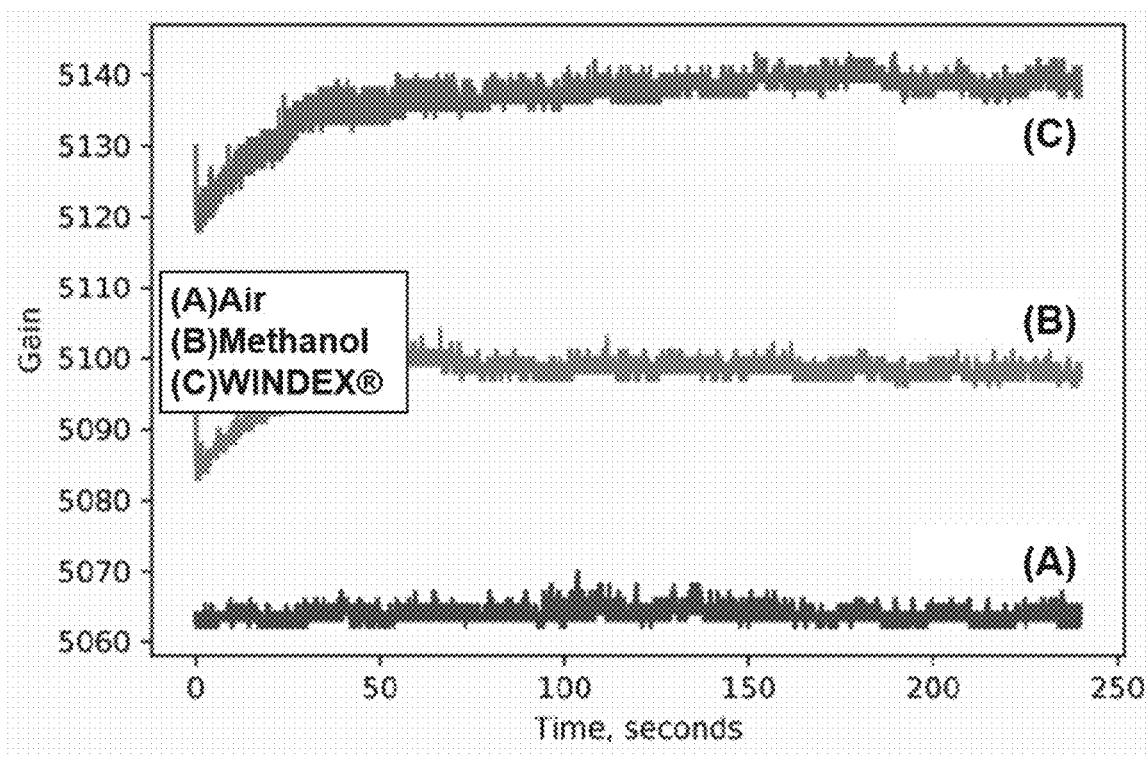
FIG. 4 is a plot showing the gain response of a clean resonator crystal to ambient air, methanol, and WINDEX®.

Using an olfactory sensor device constructed as discussed above in the Detailed Description and as shown in FIG. 1, clean resonator crystals were placed in a container in the presence of ambient air, methanol, and WINDEX®. The crystal was cycled in the following light sequence: (1) 25 seconds no light; (2) 25 seconds IR light; (3) 25 seconds UV+IR light; and (4) 25 seconds UV light. Referring now to FIG. 4, when the crystal resonator was exposed to an odorant, the gain change was plotted as a function of time. As shown in FIG. 4, the crystal resonator exhibits a gain change that saturates at a value dependent on the odorant.

Referring still to FIG. 4, the "clean" crystal resonator does not show a meaningful response to the light irradiation. Thus, it is very difficult to discriminate between chemicals through the system using a clean crystal, as the equilibrium gain value drifts slowly with time, and extra electronics would be needed to stabilize the gain. Although it is possible to stabilize the crystal's gain signature, such stabilization must be performed with care to avoid affecting the short-term dynamics of the gain change and phase change under irradiation.

Example 2. Identification of Odorants Using Nanowire-Coated Crystals

Device Preparation

Figure 5A:
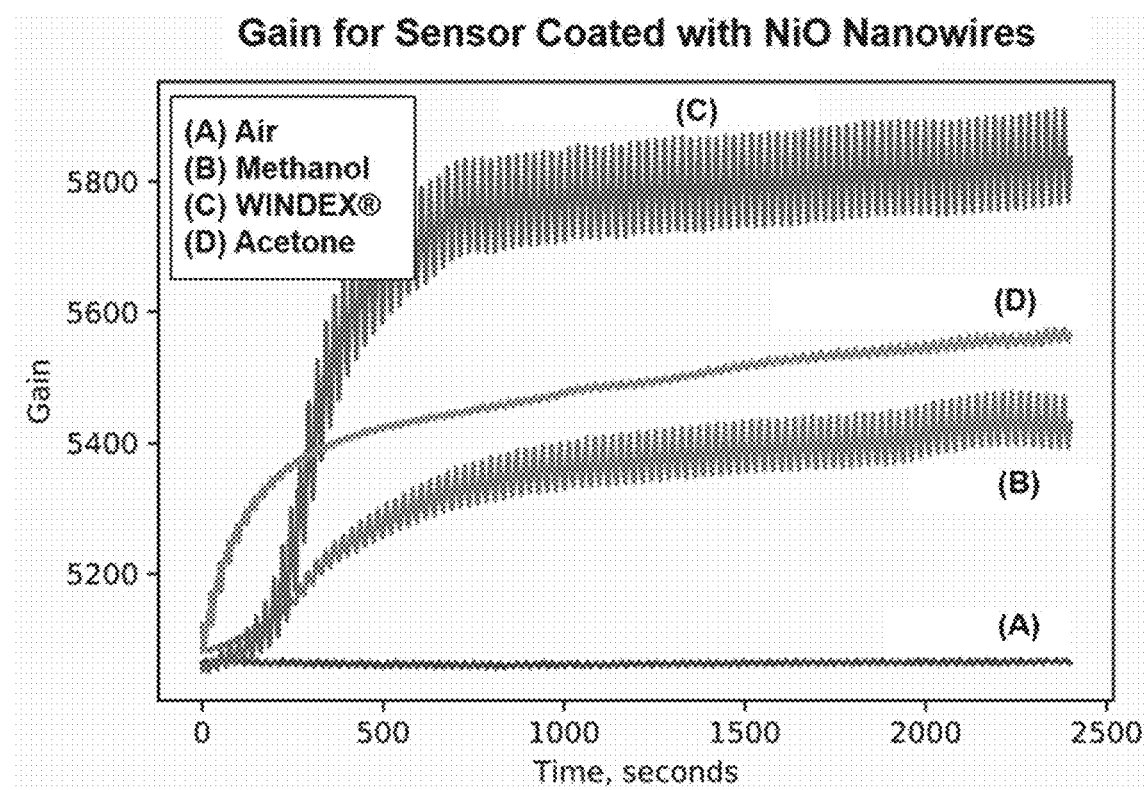
FIG. 5A is a plot showing the gain response of a resonator crystal treated with nickel oxide (NiO) nanowires in the presence of ambient air, methanol, acetone, and WINDEX®.
Figure 5B:
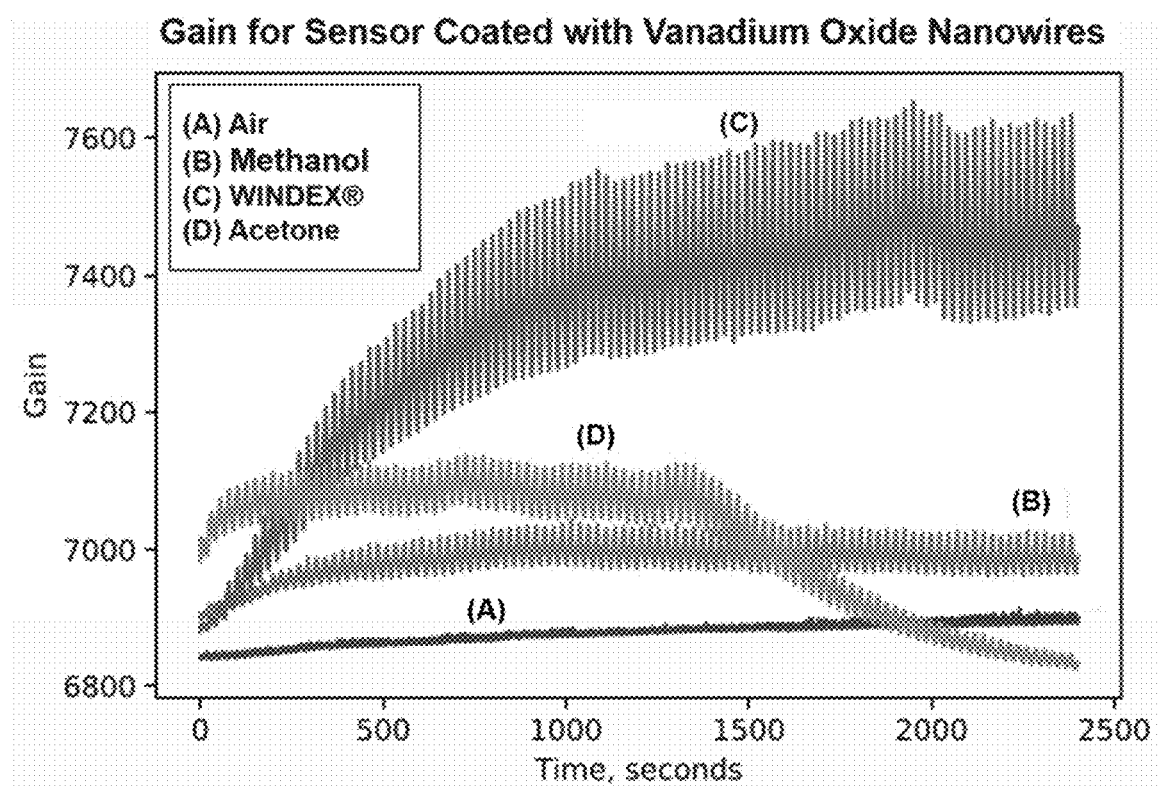
FIG. 5B is a plot showing the gain response of a resonator crystal treated with vanadium oxide ($VO_2$) nanowires in the presence of ambient air, methanol, acetone, and WINDEX®.

Referring now to FIGS. 5A, 5B, and 6, to test the ability of olfactory sensor devices according to the present disclosure to distinguish among several different odorants, olfactory sensor devices were prepared using quartz crystal resonators with modified surfaces to enhance the gain response the resonator. These devices were prepared according to the embodiment shown in FIG. 1.

To modify the sensor surface, a solution of NiO or $VO_2$ nanowires was drop-cast onto quartz crystal resonator surface and dried under ambient conditions. The gain response of a quartz crystals treated with nickel oxide (NiO) nanowires (FIGS. 5A, 6) and vanadium oxide ($VO_2$) nanowires (FIG. 5B) was measured in the presence of air, methanol, ethanol, isopropanol, acetone, mineral spirits, and WINDEX®, and under irradiation using the following light sequence: (1) 25 seconds no light; (2) 25 seconds IR light; (3) 25 seconds UV+IR light; and (4) 25 seconds UV light. The oscillations observed in the plots are attributed to the system response to the cycling ambient light. As evidenced in FIGS. 5A and 5B, the gain response depends on the particular adsorbed odorant.

Referring to FIGS. 5A and 5B, when IR and/or UV irradiate the sensor, the incident light changes the rate of odorant adsorption and desorption at the sensor surface. So, the adsorption kinetics (and the adsorbed mass of odorant over time) will depend on the incident light and the identity of the odorant. Under each unique incident light (e.g., no light, IR, UV, or UV+IR), the gain change will converge to a different equilibrium value. Thus, measuring the parameters of the convergence curve provides indirect information about the one or more odorants present in the ambient air which can be used to distinguish between odorants.

Distinguishing Between Odorants

Odorant detection methods according to the present disclosure rely on indirect measurement to identify an odorant—that is, the system needs to have "experienced" a particular odorant in order to recognize it. This is because the system provides no direct information about the chemical identity of the odorant (e.g., infrared or UV absorption peaks) and does not rely on irradiation using narrow-band IR radiation, for example. The system also does not need to scan through a wavelength range of IR or UV irradiation to obtain a spectrum indicating the particular odorant(s) present. However, it is also difficult for the system to accurately identify an odorant to which it has never been exposed.

Accordingly, a machine-learning algorithm was used to analyze the experimental results and identify odorants (see FIG. 3 and corresponding text). For each of the aforementioned odorants (see FIG. 6) and each irradiation source (e.g., no light; UV; IR; UV+IR), the parameters of a curve presenting gain and/or phase response as a function of time are recorded and fed into a model (see FIG. 3). Typically, data points from less than or equal to 100 cycles (e.g., less than or equal to 100 repetitions of the above-discussed light sequence: (1) 25 seconds no light; (2) 25 seconds IR light; (3) 25 seconds UV+IR light; and (4) 25 seconds UV light), is sufficient to build a model. The inputs to the model are parameters of the gain and phase curve response for each light, with the output being a discrete set of odorants. Various parameters can be used as inputs for analysis; for instance, curve fitting parameters from different curve fits appropriate for the data, including coefficients from polynomial curve fits (such as quadratic polynomials) or logarithmic curve fits.

Referring now to FIG. 6, seventy cycles of the above-discussed light sequence were chosen to build ("train") the model, and the remaining thirty cycles were used for model evaluations. The results presented utilize a discrete classifier algorithm Linear Discriminant Analysis (LDA), although other classifier algorithms, such as the Nearest Neighbors classifier, provide for similar results. As shown in FIG. 6, the accuracy of the model, even for the relatively low number of training examples, is between 90% and 100% (in terms of correct identifications out of 30 tests).

The above-described system and method measures no information about either frequency shift or dissipation. Thus, the method is different from the frequency shift based resonator sensors, or dissipation-based resonator sensors (QCM-D), which require time-consuming, complex procedures for measuring the response of the resonator at several frequencies surrounding the resonant frequency to determine peak location (for frequency) and width (for dissipation). In comparison with the e-nose, the difference in the hardware is in the use of the resonators which afford much faster response, and the use of different light sources (e.g., broadband UV and/or IR light) to measure the responses. Without the use of light sequences based on two or more light sources, the system saturates to a fixed value, and the output from the system is severely limited. On the other hand, cycling between two or more light sources (e.g., IR, UV, and IR+UV cycles) provides for a continuous and repeatable change in resonator response, allowing measurement of curve parameters for each irradiation. Instead of one equilibrium value, the curve parameters for four light combinations provide for at least 6-15 values for either gain or phase, which is sufficient to build a classifier for a large number of chemicals.

The information can then be used for a real-time detection of odorants, in which an odorant for which a model exists in the device's database is positioned inside the device, and the device is asked to identify the odorant. It is possible to achieve a 100% accuracy of odorant detection for 100 data points as learning examples if the number of chemicals in the database is sufficiently small (e.g., on the order of 5-10) and their structures or behavior are sufficiently diverse. If the number of odorants is much larger, the number of learning examples must also increase. It is not currently clear whether there is a fundamental limitation on the number of odorants detected. The limitation may be due to having to collect an unreasonably large number of learning examples, and thus be technological, not fundamental, in nature.

However, this technological obstacle may be circumvented by utilizing several resonators coated with different nanowires, in the same device, and simultaneously recording data from these resonators. Again, no particular nanowire coating is required, as long as the resonant frequencies of the resonators are similar and they can be driven by the same frequency simultaneously. The response of the device is different for different nanowire coatings. Thus, the number of data points collected is proportional to the number of resonators utilized.

Example 3. Measuring Odorant Concentration

To determine whether olfactory sensor devices according to the present disclosure are capable of determining odorant concentration, an olfactory sensor device was prepared and exposed to odorant vapor as described above for Examples 1 and 2. Although direct measurement of odorant concentration in ambient air requires a complex experimental system, the olfactory sensor device according to the present disclosure exhibits sensitivity to odorant concentration. In the aforementioned system, the odorant concentration in air is achieved by depositing a small open container with odorant fluid in the container, then allowing the odorant to evaporate. Several models are available for calculating the concentration of one or more odorants in air, as a function of time (e.g., logarithmic, exponential). The disclosure below relates to only one such model, and those of ordinary skill in the art will understand that other methods may be used to estimate concentration.

In some embodiments, the odorant concentration will reach the final saturation concentration co after a certain equilibration time T, with the saturation concentration dependent on the particular odorant. By way of non-limiting example, the concentration as a function of time c(t) may be determined according to Equation 1 as follows:

$$c(t) = \left(1 - e^{-\frac{t}{T}}\right)c_0, \quad (1)$$

where T is the equilibration time, and t is exposure time.

Figure 7:
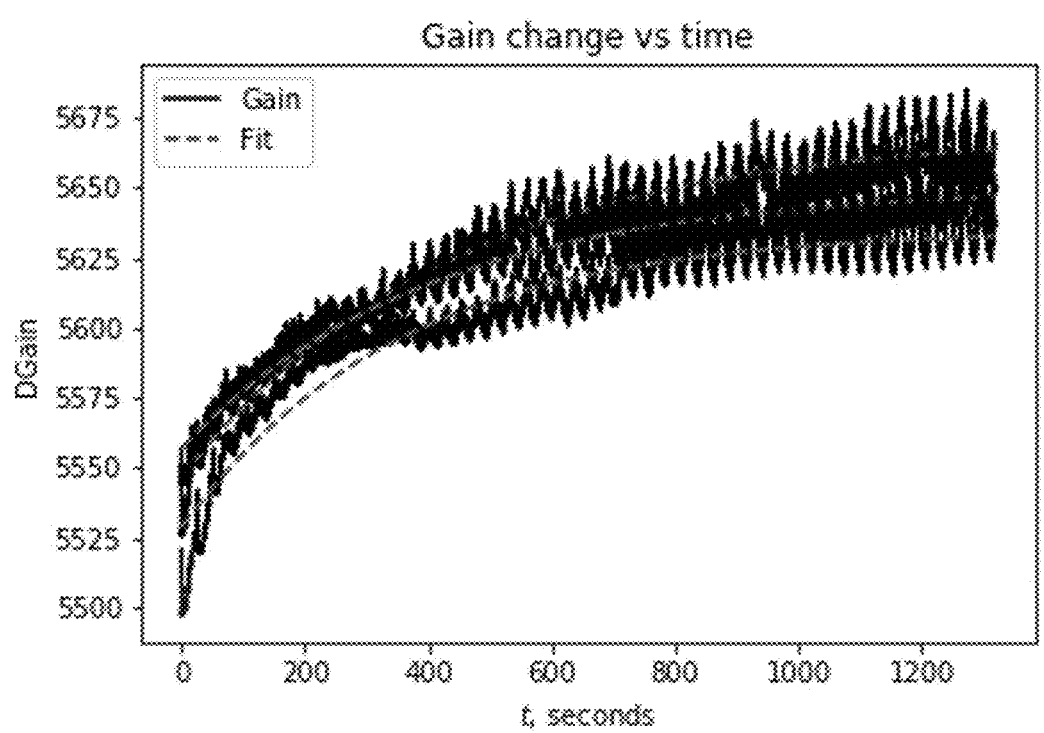
FIG. 7 is a plot of gain variation versus time for an olfactory sensor device according to the present disclosure, including a resonator crystal treated with NiO nanowires, in the presence of methanol.

Referring now to FIG. 7, assuming that the average gain change is proportional to concentration, the dependence of the gain G(t) on concentration may be calculated according to Equation 2 below:

$$G(t) = G_e + \left(1 - e^{-\frac{t}{T}}\right)G_0, \quad (2)$$

Using the net gain change given by Equation 2, changes in the parameters of the gain curves were obtained for one or more odorants, for the aforementioned light sequence: (1) 25 seconds no light; (2) 25 seconds IR light; (3) 25 seconds UV+IR light; and (4) 25 seconds UV light. The parameters were measured for each light cycle, and the time was computed as the time in the middle of the light cycle. In this experiment, the time between each light or light combination in the cycle takes about 10 seconds, and the time scale of the concentration equilibration time T is several hundred seconds. Thus, the system is able to predict the change of curve parameters for different lights as the concentration slowly increases to its equilibrium value.

Figure 8:
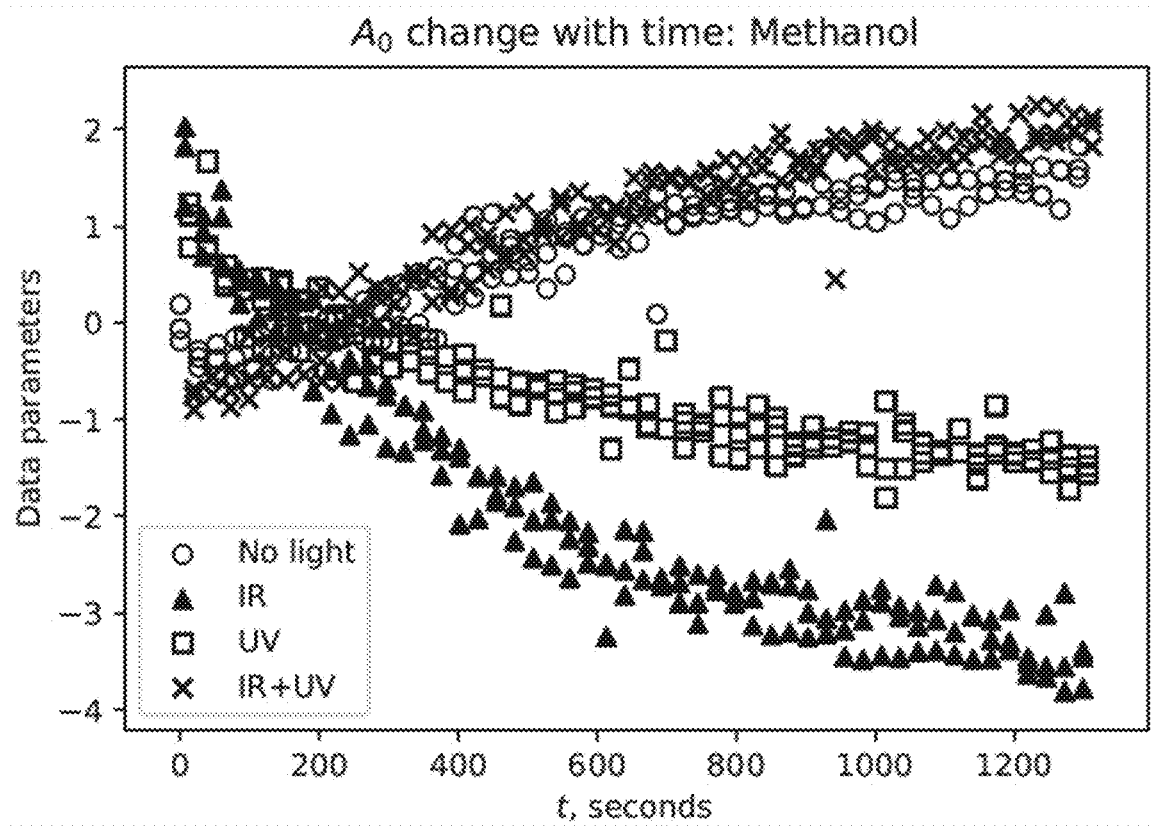
FIG. 8 is a plot of the change in curve parameter $A_0$ versus time for a resonator crystal treated with NiO nanowires, in the presence of ambient methanol, when irradiated by different light sources.
Figure 9:
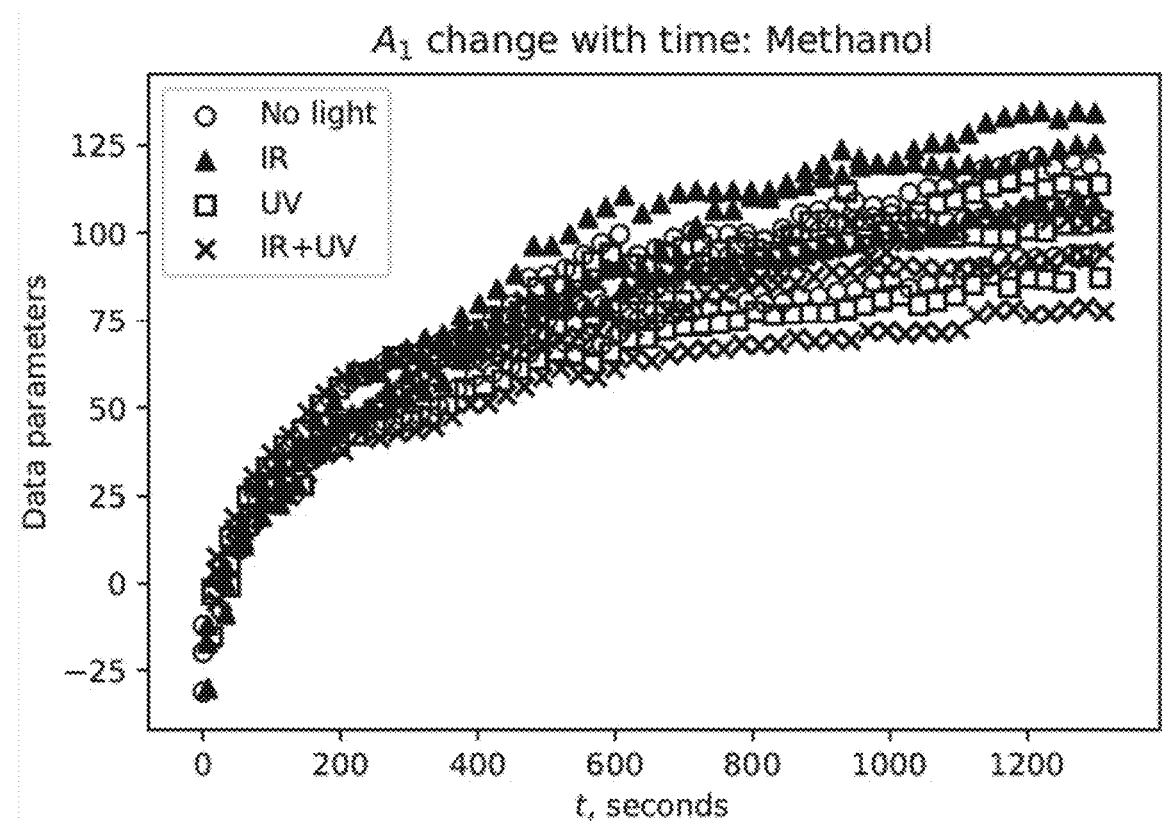
FIG. 9 is a plot of the change in curve parameter $A_1$ versus time for a resonator crystal treated with NiO nanowires, in the presence of ambient methanol, when irradiated by different light sources.
Figure 10:
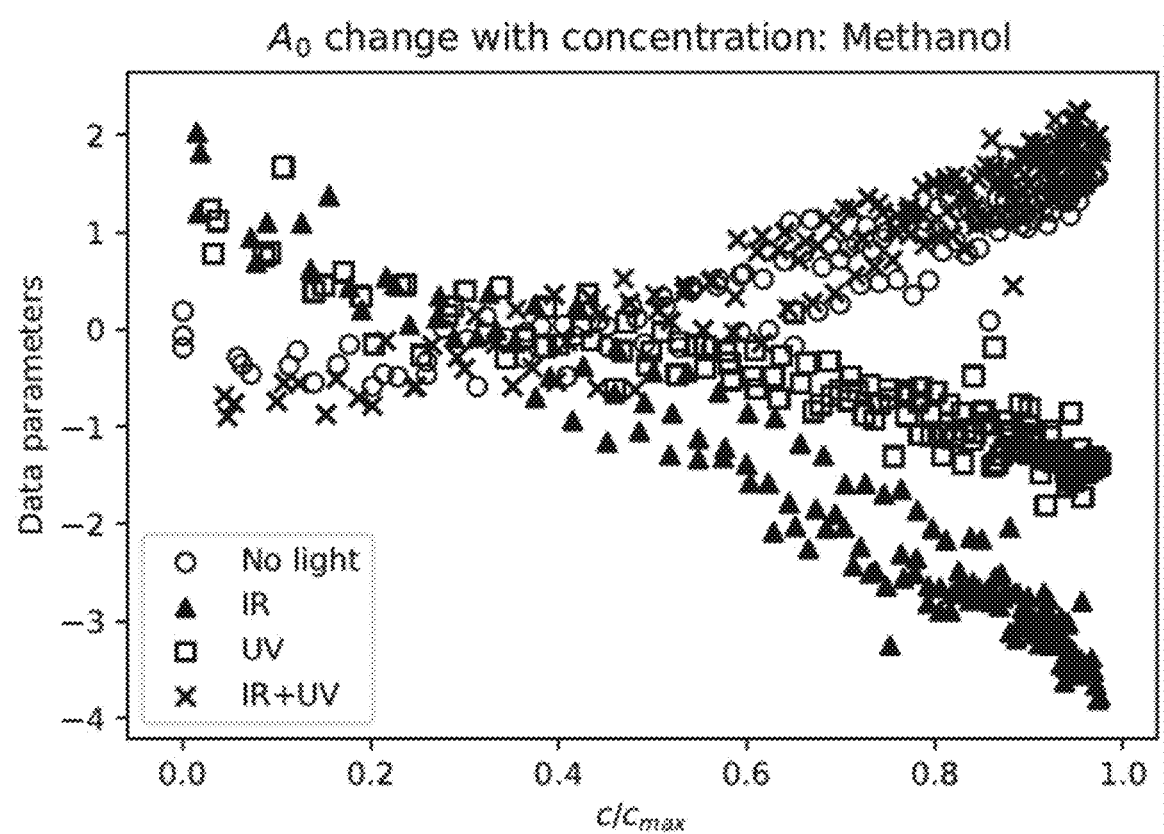
FIG. 10 is a plot of the change in curve parameter $A_0$ versus concentration for a resonator crystal treated with NiO nanowires, in the presence of ambient methanol, when irradiated by different light sources.
Figure 11:
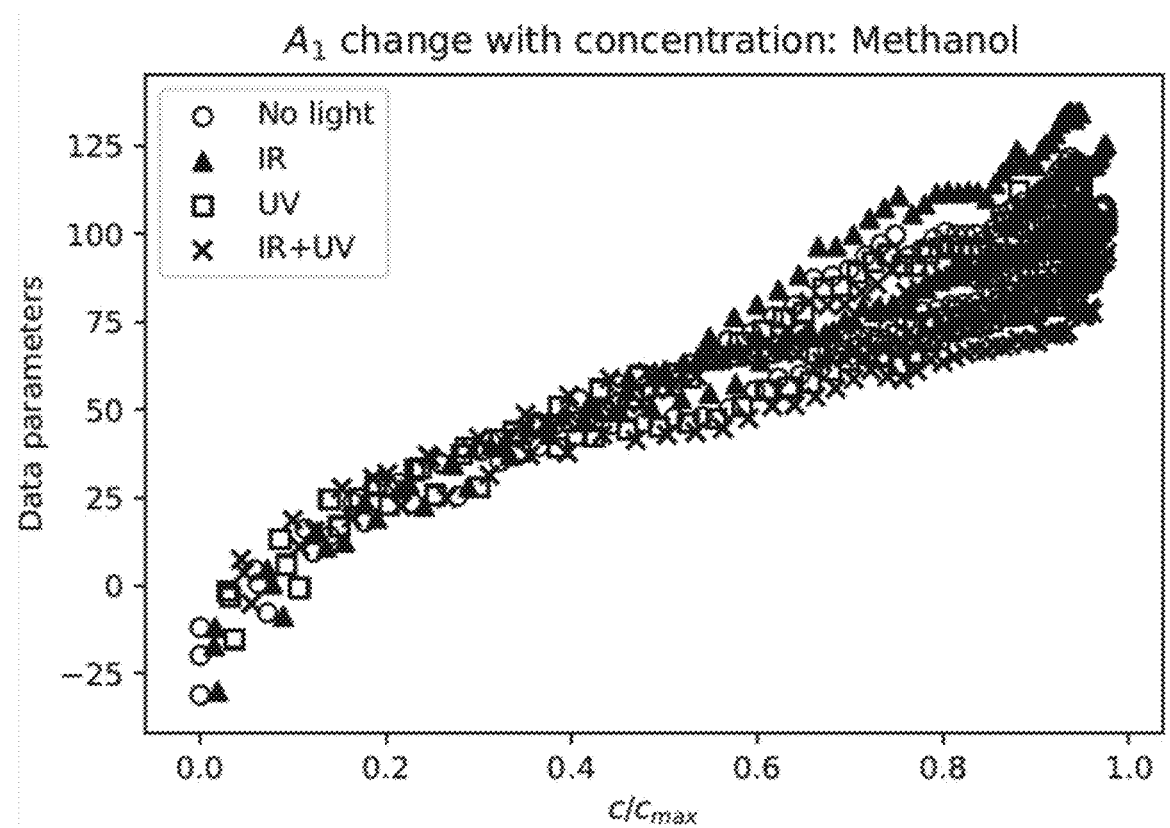
FIG. 11 is a plot of the change in curve parameter $A_1$ versus concentration for a resonator crystal treated with NiO nanowires, in the presence of ambient methanol, when irradiated by different light sources.

The change of curve parameters, for particular parameters $A_0$ and $A_1$ of the curve, are shown, for methanol, in FIG. 8 and FIG. 9, respectively. Using Equation 2, the change of curve parameters $A_0$ and $A_1$ of the curve, as a function of concentration, are shown in FIG. 10 and FIG. 11 respectively. Curve parameters $A_0$ and $A_1$ are parameters determined from a fit (e.g., a polynomial fit) of the data. In practice, various curve fitting parameters may be extracted from the data for a variety of different curve fits (e.g., logarithmic, etc.), as appropriate for a given experiment. As indicated in FIG. 10 and FIG. 11, it is possible to detect the change of concentration for a given odorant, and also to estimate odorant identity and concentration, by utilizing the combined information about the concentration and odorant identity.

Calibration Using Odorant Concentration

With regard to odorants of unknown concentration, which would almost certainly be the case in numerous field applications, olfactory sensor devices according to the present disclosure may be calibrated by inducing a "learned response" to known odorants at known concentrations, then scaling the parameters of the change in gain or change in phase curves according to the concentration.

Example 4. Wearable Device Tested During Exercise Cycle

Figure 12:
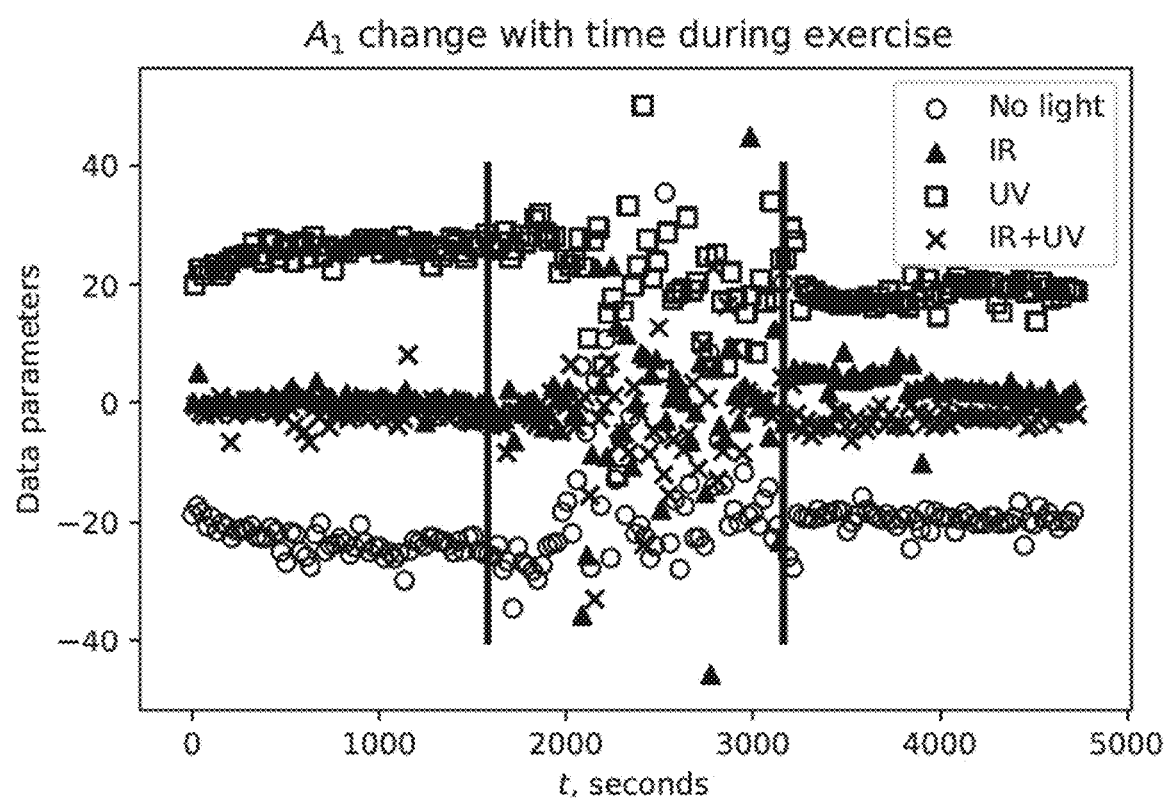
FIG. 12 is plot showing change in curve parameter $A_1$ versus time, during exercise (15 minutes rest, 15 minutes exercise: 15 minutes recovery) for an embodiment of a wearable olfactory sensor device according to the present disclosure, including a resonator crystal treated with ZnO nanowires, with the olfactory sensor device worn against the hand of a human subject, such that the sensor was exposed to air containing odorants from human skin (e.g., sweat vapor), during the entire 45-minute cycle.

Referring now to FIG. 12, to demonstrate the ability of olfactory sensor devices according to the present disclosure to determine characteristics of one or more odorants from a human subject (e.g., from sweat vapor), the olfactory sensor device prepared according to Examples 1-3 was equipped with an adjustable band, to enable a human subject to wear the device on the subject's arm or hand during exercise. FIG. 12 shows the measured change in curve parameter $A_1$ during a rest-exercise-recovery cycle (15-min rest; 15-min exercise; 15-min recovery) for an adult male human subject.

The olfactory sensor device was worn on the hand, with the sensor oriented in a manner to expose the sensor to the air in the immediate vicinity of the subject's skin (containing sweat vapor) during the entire 45-minute rest-exercise-recovery cycle. The measurement utilized the same light sequence discussed above in Examples 1 and 2. As shown in FIG. 12, it is possible to record changes in one or more physical parameters of the quartz resonator in the wearable odorant sensor. As evidenced by FIG. 12, the change in curve parameter $A_1$ is relatively static during the rest and recovery phases, while the resonator shows wide fluctuations in odorant adsorption during the exercise cycle.

Example 5. Wearable Devices for Hormone Detection in Human Subjects

Figure 13:
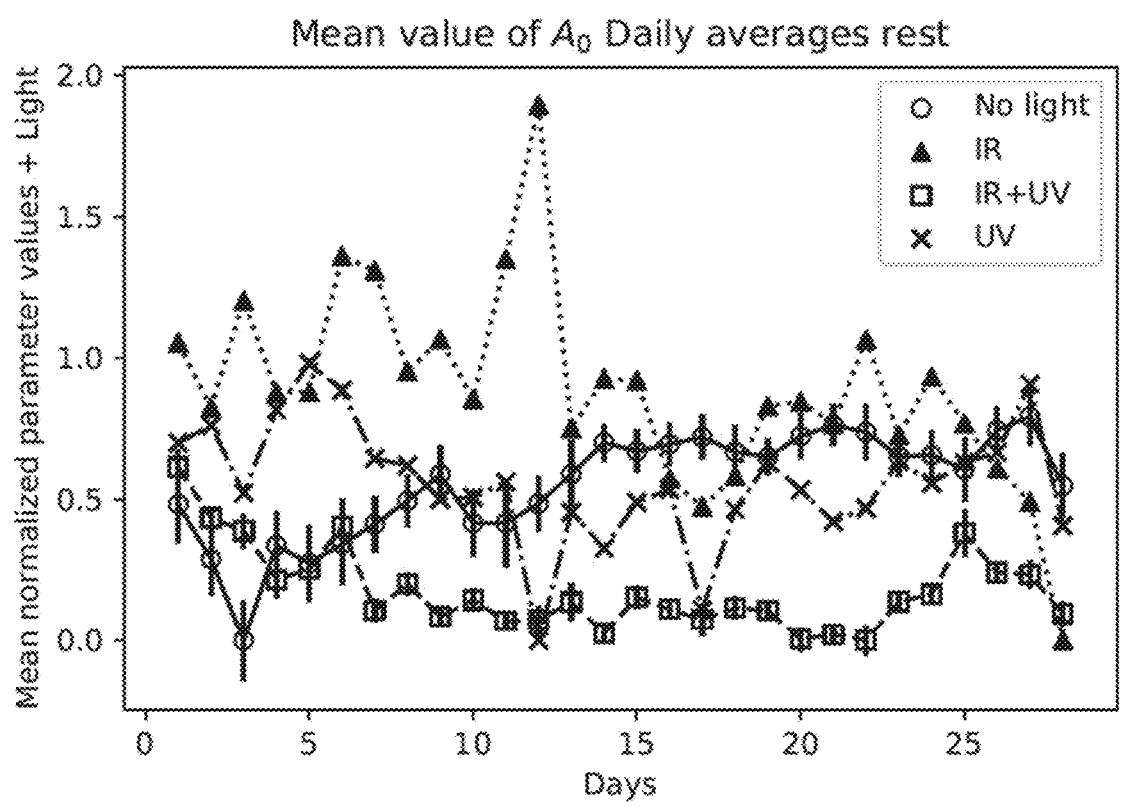
FIG. 13 is a plot showing mean normalized value of curve parameter $A_0$ versus time (in days), for a wearable embodiment of an olfactory sensor device according to the present disclosure, including a resonator crystal treated with ZnO nanowires, with the olfactory sensor device worn against the hand, with the sensor exposed to odorants in from skin of a healthy 16-year-old human female subject, for 45 minutes daily, for a total of 28 days. The subject was resting during each measurement.

Referring now to FIG. 13, to demonstrate the sensitivity of olfactory sensor devices prepared according to the present disclosure and the capability to measure the presence of odorants from human subjects (e.g., correlated with ovulation times), a wearable olfactory sensor device prepared according to the present disclosure (FIG. 1, Examples 1-4) was worn by a 16-year-old human female subject over the course of 28 consecutive days. The olfactory sensor device was worn on the subject's hand, with the sensor oriented in a manner to expose the sensor to the air in the immediate vicinity of the subject's skin (air containing sweat vapor) for a continuous 45-minute cycle each day. The data shows changes in the mean value of $A_1$, measured daily for 28 days. In particular, the green line (UV irradiation) shows peaks at maximum hormonal changes typically observed for human female subjects (e.g., for FSH, E2 and SH hormones), which are expected on days 13-17. (See generally A. Druett, Ovulation: What Is It, and How Do I Know When I'm Ovulating?, CLUE (Nov. 22, 2017).) Thus, wearable olfactory sensor devices according the present disclosure may determine one or more characteristics of one or more odorants to infer ovulation in a human subject.

Example 6. Wearable Devices for Health Applications and Other Measurements

The measured change of one or more physical properties of the sensor as a reaction of sensor to vapor composition, coupled with the data analysis applied to a database containing the data describing the change, can also be used to infer health properties of the wearer (e.g., a human subject) in wearable and health applications.

Figure 14:
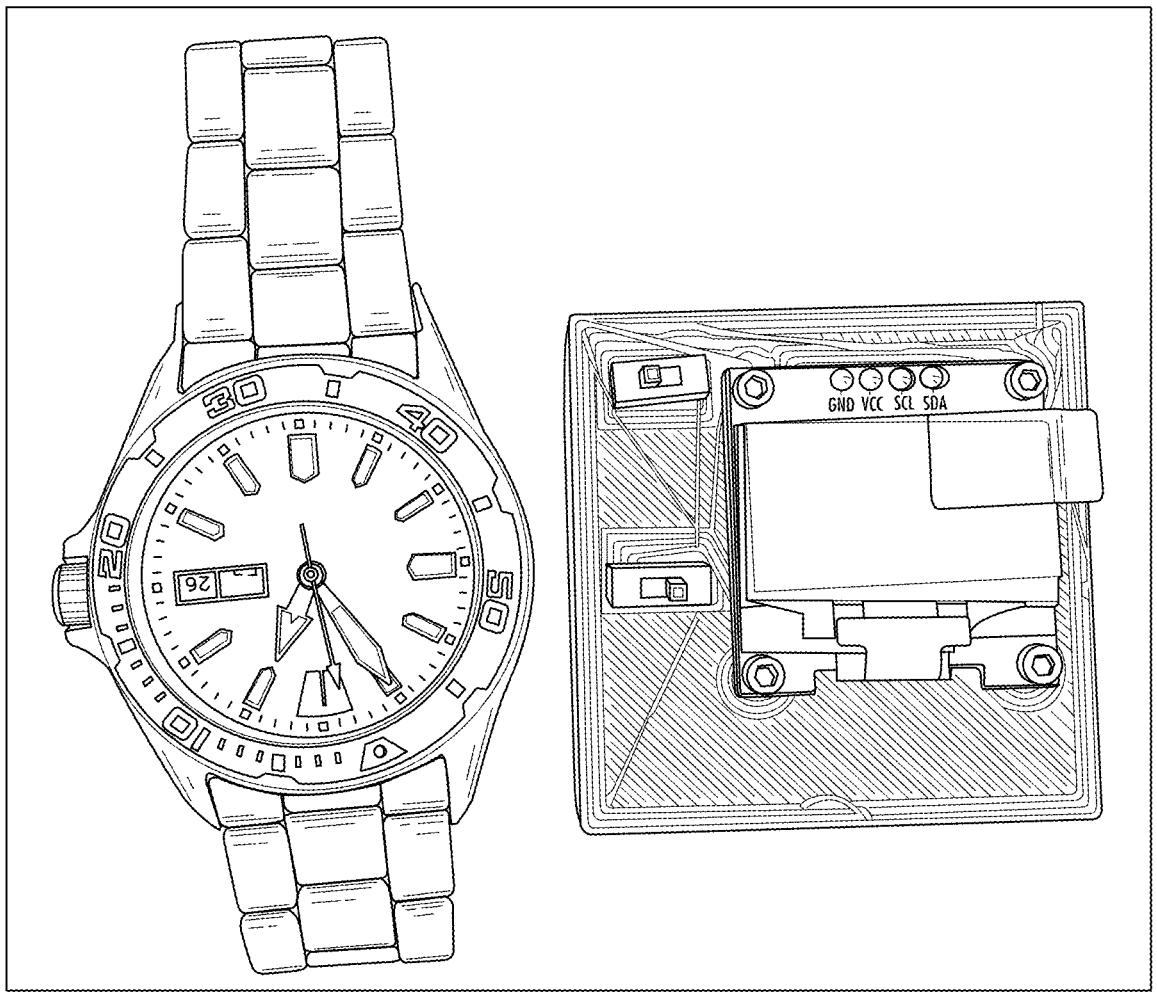
FIG. 14 is a photograph of an embodiment of a wearable olfactory sensor device (right) according to the present disclosure, shown next to a men's wristwatch (left).

Based on the demonstrated ability of wearable olfactory sensor devices ("wearable devices") according to the present disclosure to detect odorants associated with exercise or ovulation in human subjects (see Examples 4 and 5), wearable devices according to the present disclosure were tested for their ability to identify odorants in applications of interest to the health care industry. In particular, a wearable olfactory sensor device approximately the size of a men's wristwatch (FIG. 14) was constructed and used to measure blood glucose levels in a human subject.

Preparation of Wearable Olfactory Sensor Deice

FIG. 15A shows a side-view schematic of one non-limiting example of a wearable olfactory sensor device 1500 according to the present disclosure. In this embodiment of a compact wearable design, the olfactory sensor device components are enclosed within an outer housing or outer shell 1501. The outer shell 1501 comprises a top outer shell 1501a coupled to a bottom outer shell 1501b. The top outer shell 1501a may be configured to be removable from the bottom outer shell 1501b to facilitate maintenance or replacement of components contained therein. The bottom outer shell 1501b comprises an outer shell aperture 1501c configured to be positioned adjacent to a surface 1503 or oriented toward a source of one or more odorants. The surface 1503 may be any surface which emits an odorant of interest. For example, the surface 1503 may be the skin surface (e.g., on the arm) of a human subject wearing the wearable olfactory sensor device 1500. The outer shell aperture 1501c is configured to allow air comprising one or more odorants (e.g., sweat vapor) adjacent to the surface 1503 to contact a sensor 1502 positioned inside the device.

The outer shell 1501 encloses one or more electronic components, such as one or more processors (or microcontrollers comprising a processor), signal generators, signal analyzers, transistor-based light source drivers, a memory device (e.g., a microSD card holder), and other devices. Electronic components of the wearable olfactory sensor device 1500 are disposed on a custom-designed printed circuit board (PCB) 1521. Though not intended to be limiting, such configurations may be arranged as shown in, e.g., FIG. 1 or FIGS. 15A-B, using similar components, though one of ordinary skill in the art will recognize that other configurations will fall within the scope and spirit of this disclosure. Components may be arranged on the top side and bottom side of the PCB 1521.

Figure 15B:
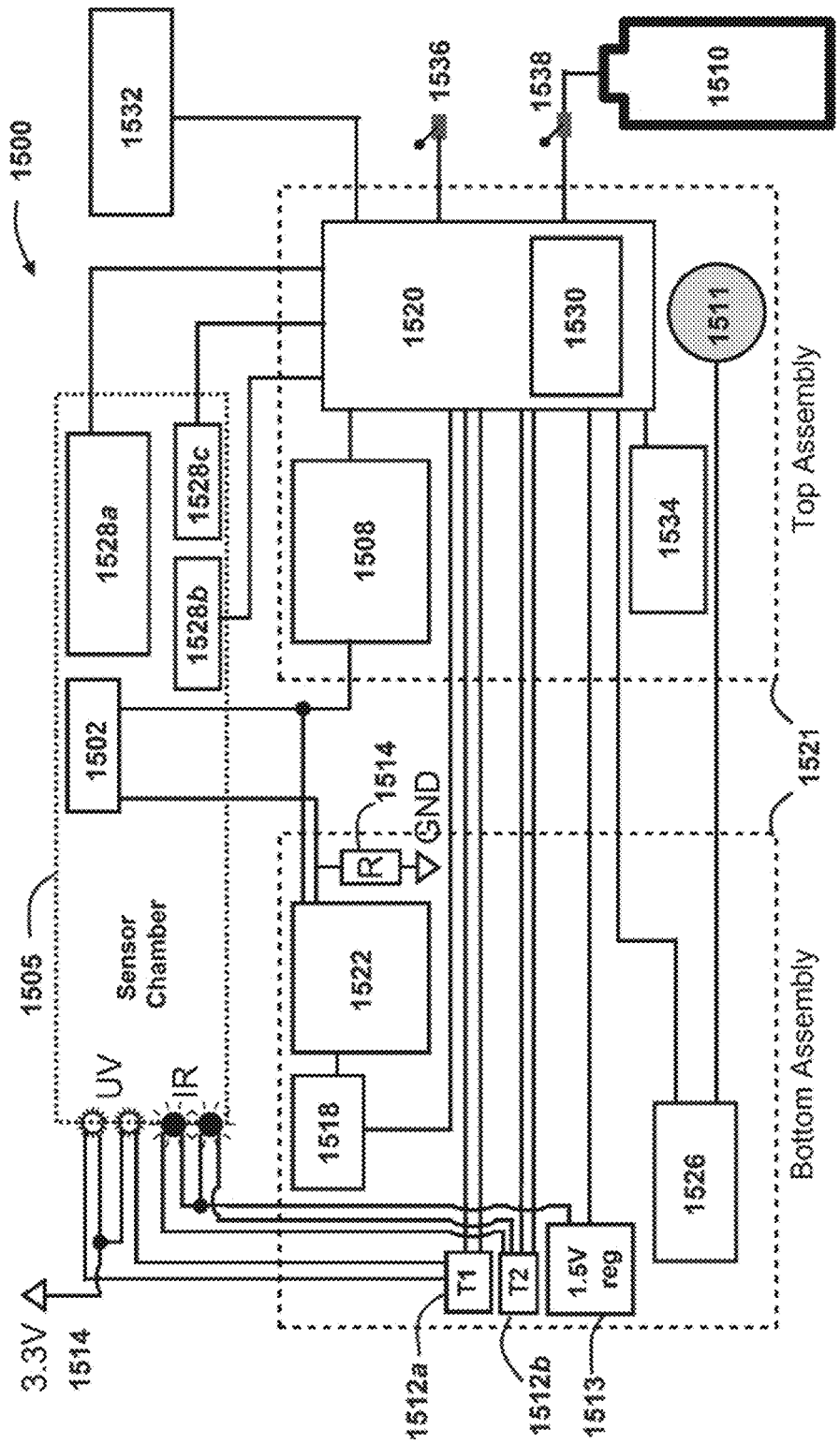
FIG. 15B is a schematic illustration showing one possible arrangement of electronic components in a wearable olfactory sensor device according to FIG. 15A.

Referring to FIGS. 15A and 15B, this embodiment of a wearable olfactory sensor device further comprises an inner shell 1505 configured to house one or more sensors 1502 and one or more light sources (e.g., two IR light sources 1504a, 1504b and two UV light sources 1506a, 1506b) inside the sensor chamber. The sensor 1502 comprises a resonator (e.g., a 4 MHz quartz crystal resonator which has a narrow resonance and high sensitivity).

The sensor 1502 is communicably coupled to a signal generator (frequency generator) 1508 which is communicably coupled to a microcontroller 1520. Microcontroller 1520 may comprise any suitable processor for powering on and off the signal generator 1508 and analyzing data from the sensor 1502. The change in physical property (e.g., gain phase, amplitude) of the sensor 1502 is measured with respect to a fixed value resistor 1514, which is communicably coupled in series with the sensor 1502. The signal generator 1508 supplies a signal to the sensor 1502 and resistor 1514 and feeds two signals to gain/phase detector 1522: an input signal and a signal from the resistor+crystal contact. The order of the resistor 1514 and sensor 1502 may be switched, but the signal input to the gain/phase detector 1522 is taken from the input at the signal generator 1508 and from the resistor-crystal contact. The gain/phase detector is communicably coupled to an analog-to-digital converter (ADC) 1518, which converts the gain/phase signal to digital form. The ADC 1518 is in turn communicably coupled to the microcontroller 1520, which receives the data from the ADC 1518 and for analysis and/or storage. Data collection by the microcontroller 1520 from the sensor 1520 and auxiliary sensors 1528 is started and stopped using a measurement start-stop switch 1536 communicably coupled to the microcontroller 1520.

Each light source is communicably coupled to a relay or switch (e.g., a transistor) 1512. In this embodiment, each transistor assembly 1512a, 1512b comprises two transistors (one for each UV light source and one for each IR light source). Each transistor is communicably coupled to a microcontroller 1520 to switch each light source on and off to produce a desired light sequence. In this embodiment, the IR light sources are communicably coupled to a 1.5 V regulator 1513 to power the IR light sources. In this embodiment, the two UV light sources are powered by a 3.3 V power source 1514. The light sources are affixed to the inner surface of the inner shell 1505 such that the light sources are disposed inside the sensor chamber with the one or more sensors 1502, which is affixed to the inner surface of the inner shell 1505.

The inner shell may be in contact with or affixed to the outer shell 1501 such that the contents of the sensor chamber are exposed to a medium (e.g., ambient air, sweat vapor, breath, etc.) comprising one or more odorants, which enters the sensor chamber through the outer shell aperture 1501c. In this wearable embodiment, the outer shell aperture 1501c is adjacent to the surface 1503, such that the outer shell is in direct contact with the surface 1503. One of ordinary skill in the art will recognize that other arrangements are within the scope and spirt of this disclosure. For instance, the outer shell aperture 1501c may be oriented toward a potential source of odorants at a known distance away (e.g., across a room) from the source.

The inner shell 1505 may further house one or more auxiliary sensor(s) 1528 (e.g., such as pressure sensors, temperature sensors, humidity sensors, accelerometers, or VOC sensors). A non-limiting example of such sensors is a BME680 sensor currently offered by Bosch. In particular, for wearable devices, in addition to the types of sensors discussed above, data collected by the sensor may be augmented and/or supplemented by data collected using, e.g., a heart rate/$O_2$ saturation sensor. Non-limiting examples of such sensors are MAX30101 or MAX30102 sensors currently offered by Maxim Integrated. In this embodiment, the auxiliary sensors comprise a heart rate/oximeter sensor 1528a, a contact sensor 1528b, and a PHTV (pressure, humidity, temperature, VOC) sensor 1528c (e.g., BME680). One of ordinary skill in the art will recognize that other such sensors are within the scope of this disclosure and may be chosen to collect any information of interest for supplementing the data collected by the sensor 1502. The auxiliary sensors 1528a,b,c are disposed inside the sensor chamber and are affixed to the inner shell 1505. Auxiliary sensors 1528a,b,c are positioned near the outer shell aperture 1501c configured to facilitate direct contact with the surface 1503, close proximity to the surface 1503, or exposure to air comprising one or more odorants adjacent to the surface 1503. The auxiliary sensors 1528a,b,c are communicably coupled to the microcontroller 1520 to power the auxiliary sensors on and off and to collect and analyze data from the auxiliary sensors. In some embodiments, the auxiliary sensor(s) 1528 may be adjacent to or in direct contact with the surface 1503.

Data obtained from the sensor 1502 and/or the auxiliary sensors 1528 by the microcontroller. The data is written to a memory device 1534 (e.g., a microSD card) for subsequent analysis off-device, or analyzed by the microcontroller 1520 communicably coupled to the sensor 1502 through the ADC 1518 and gain/phase detector 1522. The microcontroller 1520 may be any suitable processor for analyzing data collected from the sensor 1502 and any auxiliary sensors 1528. For example, in this embodiment, the processor is a Cortex M4 processor, though one of ordinary skill in the art will recognize that other suitable alternative processors fall within the scope of this disclosure. Data from the microcontroller 1520 may be streamed to an external device (e.g., a computer or smartphone) using a wireless streaming device 1530 (e.g., a Bluetooth Low Energy (BLE) device). The results of measurements or data processed by the processor 1520 may be displayed (e.g., in real time) on a display device 1532 communicably coupled to the microcontroller 1520. Display device 1532 is disposed on the outer shell 1501 such that the display is in view of the user or wearer.

This embodiment of a wearable olfactory sensor device further comprises a real-time clock (RTC) 1526 communicably coupled to the microcontroller 1520. The RTC 1526 is powered by a second battery 1511 (e.g., a 3 V button battery). The second battery does not power the microcontroller 1520. Additional battery 1511 ensures that when the power is off, the RTC 1526 continues to operate.

In this embodiment, the olfactory sensor device is powered by an internal battery 1510 (e.g., a LiPo (Lithium-Polymer) battery) disposed on the PCB 1521 through an adapter 1509 and communicably coupled with the electrical components (e.g., microcontroller 1520). External batteries may also be used. The battery 1510 is capable of powering the device for several hours. In some embodiments, the internal battery 1510 may be recharged using a USB onboard plugin (not shown). A similar plugin may be used to extract data from the memory device 1534 (e.g., microSD card) without removal of the memory device. The olfactory sensor device 1500 may be powered off and on using a battery kill switch 1538 communicably coupled to the microcontroller 1520.

The overall dimensions of a device prepared according to FIGS. 15A and 15B was approximately 46 mm×46 mm, comparable to the size of a wristwatch. This embodiment can be worn against a human subject's skin. (See FIG. 14.)

Training the Machine Learning Model for Blood Glucose Measurement

Figure 16:
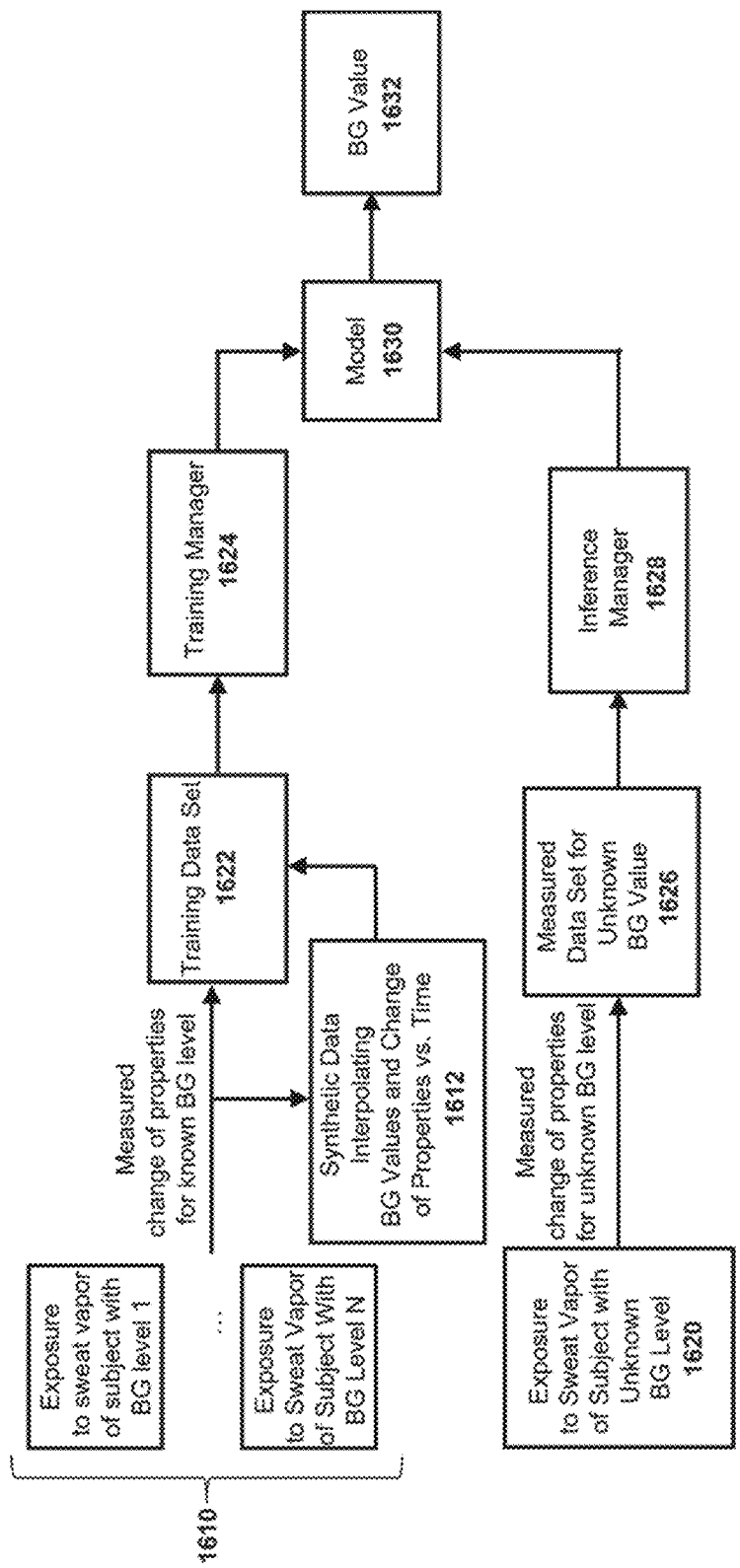
FIG. 16 is a block diagram of a machine learning process for an embodiment of an olfactory sensor device, for the detection of blood glucose levels in a human subject.

Referring now to FIG. 16, the machine learning model used for measuring continuous variables (e.g., blood glucose) is similar to that shown in FIG. 3. A machine learning model 1630 maintained by one or more processors includes a training manager 1624. The training manager 1624 trains the model 1630 based on a training data set 1622, which includes measurements of the wearer's blood glucose level 1610, taken using the consumer-level fingerpick blood glucose device, as well as linear interpolations in time between the measurements 1612. Model 1630 is constructed by using the information of multitude of fitting parameters for the wearer and, possibly, the input from the auxiliary sensors. For an unknown blood glucose level, the sensor is exposed to sweat vapor of a subject with an unknown blood glucose level 1620, and changes in the physical properties of the sensor are measured to produce a measured data set for the unknown blood glucose value 1626. The model includes an inference manager 1628 configured to apply the measured data set 1626 (e.g., a measured data set for an unknown blood glucose value), to the model 1630. The model 1630 is designed to produce the output of blood glucose level 1632 using such methods as Deep Learning, curve-fitting, interpolation and others.

Blood Glucose Monitoring Using Wearable Olfactory Sensor Deice

To demonstrate application of wearable olfactory sensor devices of the present disclosure to applications relevant to health care (e.g., detection of blood glucose level), a wearable olfactory sensor device was prepared according to FIGS. 15A and 15B and the corresponding text. The device was placed on the arm of a healthy 50-year-old human male subject. The subject was subjected to blood glucose testing while wearing the device and using a consumer-grade blood-draw blood glucose measurement device (ASCENCIA BAYER CONTOUR NEXT EZ® blood glucose meter). To maximize variability of the subject's blood glucose, a series of tests was performed at various times throughout the day. Each test consisted of measuring glucose level during 45 minutes of exercise, including varying intervals between exercise and food consumption. The blood glucose level was measured before and after each exercise interval using the commercial blood-draw device (by "finger prick") and associated blood glucose measurement strips. The change of blood glucose during exercise was interpolated based on the "before" and "after" measurements.

Figure 17:
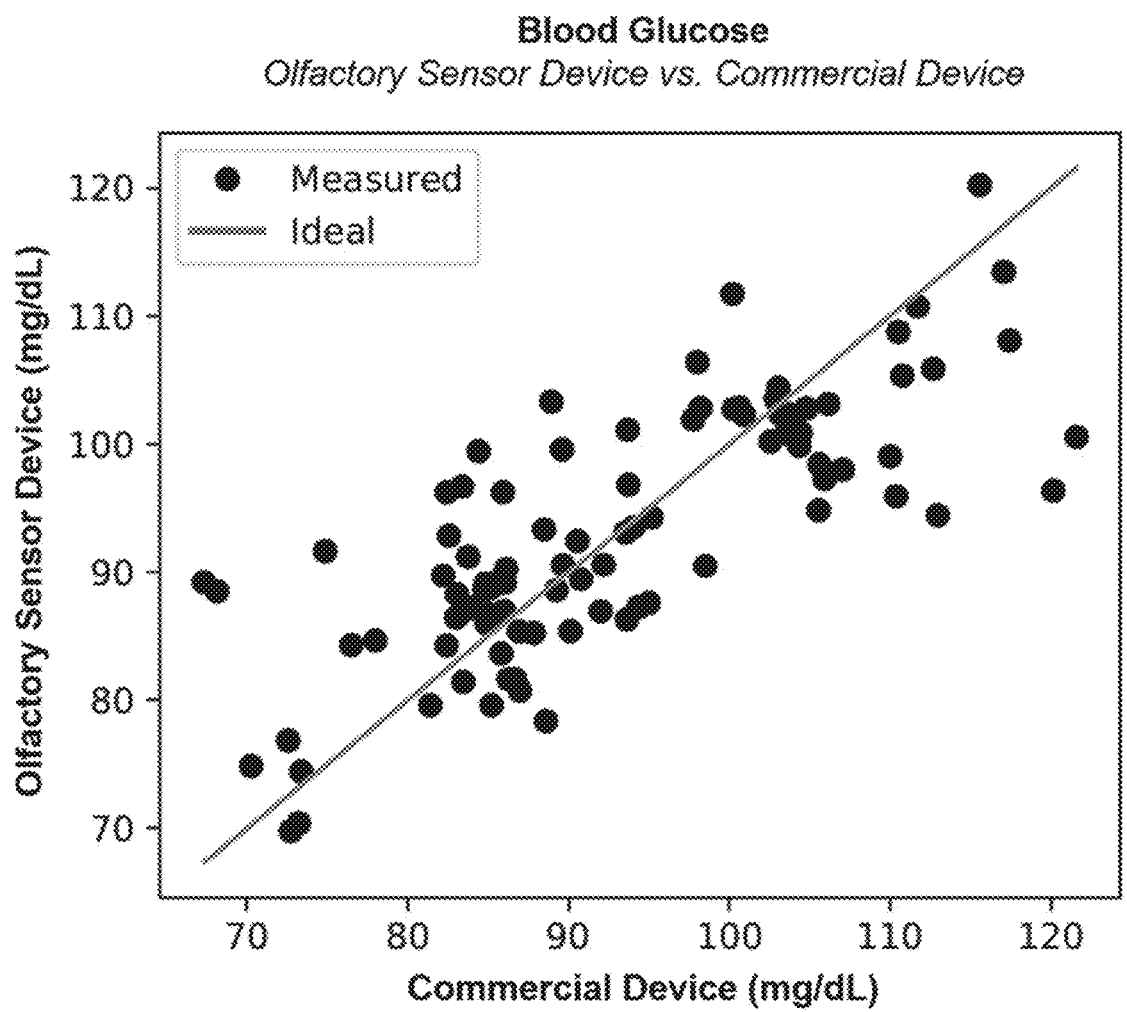
FIG. 17 shows a plot of blood glucose (mg/dL) measured using a wearable olfactory sensor device according to the present disclosure versus the blood glucose (mg/dL) measured using a commercial reference device.

At the same time as the commercial test measurements, comparative measurements were taken using the olfactory sensor device attached to the subject's upper arm. The data from blood glucose device and the wearable olfactory sensor device were correlated using a machine learning algorithm, with part of the data used for training the machine learning model and the remainder of the data used for testing. Referring now to FIG. 17, the results of the blood glucose level estimated from the wearable olfactory sensor device are compared the blood glucose levels measured using the Ascencia Bayer device. The solid line represents a (hypothetical) perfect agreement between the values obtained by the wearable olfactory sensor device and the commercial device. Accuracy of the blood glucose measurement obtained using the wearable olfactory sensor device, relative to the value obtained using the commercial device, was within approximately 9%, which is close to the ideal accuracy of consumer-grade blood glucose measuring devices.

Wearable devices according to the present disclosure may also be used to identify one or more odorants as part of an overall health monitoring regime. For instance, wearable devices may be used to identify odorants which can be used as indicators of overall health (e.g., versus baseline) when used over extended periods of time (e.g., days, weeks, months) and using different time intervals (e.g., daily, weekly, or monthly wear). Wearable devices are attractive candidates for medical diagnostic and health monitoring tools because they are relatively cheap and non-invasive. Wearable devices according to the present disclosure may also be used for animals (e.g., pets) to assess their ability to identify odorants associated with disease in animals or to monitor animal health (e.g., in the manner discussed above).

Example 7. Devices for Public Health Monitoring

Wearable devices according to the present disclosure may be used to identify odorants of interest for preventing the spread of diseases (e.g., for detection of odorants that attract mosquitoes, for use in preventing the spread of malaria). Wearable or stationary devices according to the present disclosure may also be used to determine the presence of "hidden" infections of particular public health interest, such as diseases that may go unnoticed and which may be transmitted by asymptomatic individuals or patients (e.g., COVID-19, HIV/AIDS, influenzas, tuberculosis, typhoid, etc.).

For instance, olfactory sensor devices according to the present disclosure may be used to identify odorants which may be indicators of infection with HIV, SARS-CoV-2 (COVID-19), influenzas, or any of the above-mentioned diseases/infections in human subjects. In such embodiments, machine learning models for detection of one or more diseases may be trained using a training data set comprising measurements of one or more physical properties of a sensor when exposed to, e.g., breath or sweat vapor, from human subjects whose disease status (positive or negative) is known.

Thereafter, testing an individual's disease status may comprise: exposing a sensor to one or more odorants (e.g., from the sweat vapor or breath of an individual whose disease status is unknown) to adsorb molecules of the one or more odorants onto the sensor surface; irradiating the sensor with a light sequence using one or more light sources to alter the adsorption kinetics of the molecules of the one or more odorants onto the sensor surface; measuring a change in one or more physical properties of the sensor during the irradiation, determining one or more characteristics of the one or more odorants based on the measured change during the irradiation. In such embodiments, the one or more characteristics may be the identification of one or more odorants indicating a positive (or negative) test for infection or the concentration of such odorants. In some embodiments, such methods may further comprise inferring disease status from the one or more determined characteristics.

Similar methods may be used to identify one or more odorants indicative of an acute health condition (e.g., cardiac events, sepsis, stroke) or a more slowly developing long-term health condition (e.g., kidney disease, Alzheimer's Disease, diabetes, cancer, etc.). In such embodiments, the olfactory sensor device may be disposed on a surface in a setting where one or more individuals at risk of suffering an acute health condition (or suspected of being at risk for suffering an acute health condition) or at risk of developing a long-term health condition (or suspected of being at risk thereof) are situated. For example, in these embodiments, olfactory sensor devices may be placed on or affixed to a table or other surface (e.g., a wall) in a hospital room, an adult care or nursing home facility, or in a home. In these embodiments, one or more olfactory sensor devices may be in communication (wired or wireless communication) with a notification system (e.g., an alarm, a display, a paging system) configured to notify health professionals or caretakers of an acute health event or development of a long-term health condition. Thus, when the olfactory sensor device determines one or more characteristics (e.g., identity, concentration) of one or more odorants indicating an acute health condition or progressive development of a long-term condition, the olfactory sensor device communicates a message (e.g., alarm, text message, phone call, message on a remote display) to a patient, health professional, or caretaker to facilitate early detection and intervention.

In other embodiments, wearable and/or stationary devices can be used to identify odorants useful as indicators the spread of infection, when used over extended periods of time (e.g., days, weeks, months) and using different time intervals (e.g., daily, weekly, or monthly). Wearable and/or stationary devices are attractive candidates for public health monitoring tools because they are relatively cheap, non-invasive, and can be readily deployed, as single devices in settings suitable for monitoring individual infection or, as multiple networked devices as part of a pubic monitoring system (e.g., in mass transit stations or places where large numbers of people gather, such as sporting event venues). In these embodiments, one or more olfactory sensor devices may be in communication with a notification system (e.g., an alarm, a display, a paging system, a cloud-based data collection system) configured to track spread of disease and notify public health officials if one or more odorants indicating a public health threat are detected. Thus, when the olfactory sensor device determines one or more characteristics (e.g., identity, concentration) of one or more odorants indicating a disease of interest to public health, one or more olfactory sensor devices communicate a message (e.g., alarm, text message, phone call, message on a remote display, etc.) to cloud-based tracking system or to public health officials to facilitate early detection and intervention, or to particular wearers to encourage precautionary measures (e.g., quarantine or follow-up testing).

Example 8. Devices for Use in Sports Performance Evaluation

Olfactory sensor devices according to the present disclosure may be used to evaluate the physical condition or status of an athlete by continuously monitoring the performance, vital signs, overall physical well-being, and or conditioning level of the athlete. For instance, wearable devices according to the present disclosure may be used to identify odorants useful for monitoring athlete performance, injury status, overall health, and/or conditioning level during off-season training, in-season training, or during competition. Such information could be further used to optimize the composition or make-up of athletics teams for an entire season, for a single game, or during particular stretches of individual games/matches. For instance, such information could be valuable in optimizing timing of player substitutions, offensive/defensive player matchups, or depth charts for particular games/matches.

For instance, olfactory sensor devices according to the present disclosure may be used to identify odorants which may be indicators of fatigue or injury status in athletes. In such embodiments, machine learning models for detection of one or more odorants associated with fatigue or injury may be trained using a training data set comprising measurements of one or more physical properties of a sensor when exposed to, e.g., breath or sweat vapor, from human subjects whose fatigue or injury status is known.

Thereafter, testing a subject's fatigue or injury status may comprise: exposing a sensor to one or more odorants (e.g., from the sweat vapor or breath of an individual whose fatigue or injury status is unknown) to adsorb molecules of the one or more odorants onto the sensor surface; irradiating the sensor with a light sequence using one or more light sources to alter the adsorption kinetics of the molecules of the one or more odorants onto the sensor surface; measuring a change in one or more physical properties of the sensor during the irradiation; determining one or more characteristics of the one or more odorants based on the measured change during the irradiation. In such embodiments, the one or more characteristics may be the identification of one or more odorants indicating an injury or fatigue, or the concentration of such odorants. In some embodiments, such methods may further comprise inferring fatigue or injury status from the one or more determined characteristics.

In such embodiments, wearable olfactory sensor devices may be worn by athletes training or competing in a sporting event. For example, in these embodiments, olfactory sensor devices may be worn on the athletes skin (arm, leg, shoulder, chest, back, etc.) or oriented such that the sensor is exposed to the athlete's exhalation. In these embodiments, the olfactory sensor device may be in communication with a notification system (e.g., an alarm, a display, a paging system) configured to notify an athlete, trainer, or coach of each athlete's fatigue or injury status. Thus, when the olfactory sensor device determines one or more characteristics (e.g., identity, concentration) of one or more odorants indicating fatigue or injury, the olfactory sensor device communicates a message (e.g., alarm, text message, phone call, message on a remote display) to an athlete, coach, or trainer to optimally time substitutions, adjust strategy, or adjust training regimen in real time.

Example 9. Devices for Use in the Infant Care and Elder Care Industries

Olfactory sensor devices according to the present disclosure may also be used in the care of infants (e.g., at medical or day care facilities) and of elderly people (e.g., at medical or assisted living facilities) to improve monitoring and responsiveness in routine care. For example, wearable or stationary devices according to the present disclosure may be used to identify odorants associated with diaper soiling. In this scenario, olfactory sensor devices according to the present disclosure could be used to alert caregivers, improving the responsiveness and overall quality of care.

For instance, olfactory sensor devices according to the present disclosure may be used to identify odorants indicating an acute health event (discussed above) or soiling of a diaper. In such embodiments, machine learning models for detection of one or more odorants associated with diaper soiling or an acute health event may be trained using a training data set comprising measurements of one or more physical properties of a sensor when exposed to, e.g., breath or sweat vapor, from human subjects whose acute health status is known or from ambient air in rooms containing soiled diapers.

Thereafter, monitoring a care environment may comprise: exposing a sensor to one or more odorants (e.g., from the ambient air in a room in an infant care or elder care facility) to adsorb molecules of the one or more odorants onto the sensor surface; irradiating the sensor with a light sequence using one or more light sources to alter the adsorption kinetics of the molecules of the one or more odorants onto the sensor surface; measuring a change in one or more physical properties of the sensor during the irradiation; determining one or more characteristics of the one or more odorants based on the measured change during the irradiation. In such embodiments, the one or more characteristics may be the identification of one or more odorants indicating an acute health event or soiling of a diaper. In some embodiments, such methods may further comprise inferring the occurrence of an acute health event or the soiling of a diaper.

In these embodiments, olfactory sensor devices may be placed on or affixed to a table or other surface (e.g., a wall) in an infant care, child care, or elder care facility, or in a home. In these embodiments, one or more olfactory sensor devices may be in communication with a notification system (e.g., an alarm, a display, a paging system) configured to notify health professionals or caretakers of an acute health event, soiling of a diaper, or other event. Thus, when the olfactory sensor device determines one or more characteristics (e.g., identity, concentration) of one or more odorants indicating an acute health event or soiling of a diaper, the olfactory sensor device communicates a message (e.g., alarm, text message, phone call, message on a remote display) to a health professional or caretaker to facilitate early intervention.

Example 10. Devices for Use in the Hospitality and Travel Industries

Olfactory sensor devices according to the present disclosure may be used to identify odorants associated with illicit activity (e.g., illegal drug use), smoking, the presence of allergens, cleanliness (e.g., cleanliness of bathrooms) to improve quality of service and facilities in the hotel, car rental, and restaurant industries. For example, olfactory sensor devices placed in hotel rooms, rental cars, vacation rental homes (e.g., Airbnb rentals), apartments, and restrooms (e.g., in restaurants) could alert property owners or custodians as to unsanitary conditions or to ongoing illicit activity, allowing property owners to more quickly remedy unsanitary conditions or to alert law enforcement as to illegal activity.

For instance, olfactory sensor devices according to the present disclosure may be used to identify odorants associated with illicit activity or unsanitary conditions. In such embodiments, machine learning models for detection of one or more odorants associated with illicit activity or unsanitary conditions may be trained using a training data set comprising measurements of one or more physical properties of a sensor when exposed to, e.g., ambient air in a hotel room, rental car, or restaurant, where the presence of one or more odorants associated with illicit activity or unsanitary conditions is known.

Thereafter, monitoring an environment of interest to the hospitality or travel industry (e.g., hotel rooms, rental cars, vacation rental homes, apartments, and restrooms (e.g., in restaurants)) comprises: exposing a sensor ambient air from an environment of interest to the hospitality or travel industry to adsorb molecules of the one or more odorants onto the sensor surface, irradiating the sensor with a light sequence using one or more light sources to alter the adsorption kinetics of the one or more odorants onto the sensor surface; measuring a change in one or more physical properties of the sensor during the irradiation; determining one or more characteristics of the one or more odorants based on the measured change during the irradiation. In such embodiments, the one or more characteristics may be the identification of one or more odorants indicating illicit activity or unsanitary conditions. In some embodiments, such methods may further comprise inferring the occurrence illicit activity or unsanitary conditions.

In these embodiments, olfactory sensor devices may be placed on or affixed to a table or other surface (e.g., a wall) in an environment of interest to the hospitality or travel industry (e.g., hotel rooms, rental cars, vacation rental homes, apartments, and restrooms (e.g., in restaurants)). In these embodiments, one or more olfactory sensor devices may be in communication with a notification system (e.g., an alarm, a display, a paging system) configured to notify hospitality workers, travel industry workers, property owners, or law enforcement of illicit activity or unsanitary conditions. Thus, when the olfactory sensor device determines one or more characteristics (e.g., identity, concentration) of one or more odorants indicating illicit activity or unsanitary conditions, the olfactory sensor device communicates a message (e.g., alarm, text message, phone call, message on a remote display) to one or more hospitality or travel industry workers to facilitate early intervention and improvement of the unsanitary condition(s).

Example 11. Devices for Use in Agriculture and the Food Industry

Olfactory sensor devices according to the present disclosure may be used to detect odorants of importance in agriculture and in food production. For instance, olfactory sensor devices may identify odorants associated with food growth and production (e.g., to determine optimum harvesting times or for early detection of disease in a crop); in food processing and/or shipping scenarios (e.g., for detection of odorants associated with rotting fruit and/or vegetables); in food storage and point-of-sale scenarios (e.g., for verifying odorants associated with rotting and/or fresh food in grocery stores, restaurants, bars, etc.).

In other contexts, olfactory sensor devices may be used to identify one or more characteristics of odorants indicative of food quality or to determine whether food products merit a given certification (e.g., whether a given food product is "organic" or "vegan") or geographical indication (e.g., "champagne," "Parma ham," or "Gorgonzola cheese"). In addition, olfactory sensor devices may be used to identify odorants that indicate the quality or origin of wine, whiskey, or other fine beverages. Further, olfactory sensor devices may be used for determining whether foods qualify for certain trade designations (e.g., "organic foods" which do not evidence the presence of one or more odorants associated with the use of pesticides)

Olfactory sensor devices according to the present disclosure may be used in agricultural settings related to the production of meat and dairy products. For instance, olfactory sensor devices may be used to identify odorants associated with animal reproduction (e.g., cattle or pig ovulation) to determine optimum timing for breeding livestock; their ability to identify odorants indicating hazardous living conditions where livestock and/or poultry are kept (e.g., detecting rising levels of ammonia in chicken coops); and/or their ability to identify odorants associated with the spread of disease among livestock (e.g., within a herd of cattle).

Example 12. Devices for Use in Occupational Health and Safety and/or Environmental Testing Olfactory sensor devices according to the present disclosure may be used to identify odorants indicating safety hazards (e.g., $H_2S(g)$, $NO_x(g)$) in industrial settings (e.g., factories, chemical production facilities, mines, oil and gas production facilities, etc.). Olfactory sensor devices according to the present disclosure may be used to identify odorants associated with environmental contamination (e.g., the presence of pollutants, ozone, pathogens, allergens, etc.). Olfactory sensor devices according to the present disclosure may be used to identify odorants indicating hazardous conditions in the delivery of natural gas (e.g., gas leaks in residential areas, production facilities, or pipelines) or petrochemicals (e.g., leaks in gasoline storage tanks).

In principle, a network of olfactory sensor devices (e.g., 10-100 devices) in communication with each other or in communication with a central monitoring system may be positioned throughout an industrial setting (mine, factory, power plant, laboratory, etc.) to facilitate locating the source of a hazardous leak or chemical spill, based on determining the identity and concentration of one or more odorants associated with a hazardous substance leak or spill.

Example 13. Devices for Quality Control for Consumer Goods

Olfactory sensor devices according to the present disclosure may be used to identify odorants associated with quality or product identification in consumer goods, e.g., the cosmetics and fragrances industry (e.g., to determine quality or identification of designer fragrances or to identify counterfeit goods).

Example 14. Devices for Use in the Automotive Industry

Olfactory sensor devices according to the present disclosure may be used to identify odorants associated with vehicle performance and/or vehicle maintenance issues. For instance, olfactory sensor devices may be used to identify odorants indicating leaking fluids (e.g., oil, brake fluid, coolant) under the hood of a car; odorants indicating optimum or sub-optimum engine function (e.g., as indicated by exhaust composition); or odorants indicating contaminant levels in exhaust. In these embodiments, one or more olfactory sensor devices may be in communication with a notification system (e.g., an indicator light, an alarm, etc.) to notify the driver, owner, or maintenance professional about a suspected or confirmed vehicle malfunction.

Example 15. Devices for Use in the Equestrian or Horse/Dog Show Industries

Olfactory sensor devices according to the present disclosure may be used to identify the presence of one or more odorants associated with animal health (e.g., physical condition of horses before races or equestrian events, hormone levels associated with optimum breeding times, or for the advance detection or prevention of disease in dogs). In these embodiments, one or more olfactory sensor devices may be in communication with a notification system (e.g., an indicator light, an alarm, etc.) to notify an animal owner, trainer, veterinarian, or show official about a suspected or confirmed disease, injury, fertility (ovulation), or overall health condition. These applications are of particular interest for the horse and dog show industry, livestock rearing, veterinary settings, as well as in horse racing and equestrian activities.

Example 16. Devices for Use by Government, Law Enforcement, and Regulatory Authorities Olfactory sensor devices according to the present disclosure may be used to identify odorants associated with law enforcement activities (e.g., enhancing lie detector tests by detecting and identifying odorants associated with perspiration from human skin, which may be associated with lying); odorants associated with illicit activities (e.g., odorants associated with meth labs or odorants emitted by drug users); odorants associated with explosives, pathogens, or hazardous chemicals (e.g., for use by the military to identify IEDs, use in security at mass transit facilities such as airports and subway stations, or use by public health, regulatory, or national security officials).

The present disclosure has described the use of various features and methods for detecting odorants. It should be understood that any combination of such features and methods are within the scope of the present disclosure. For example, an embodiment that describes the use of a quartz crystal resonator as the sensor for an olfactory sensor device using broadband IR and broadband UV light may be modified use a metallic sensor, and such modification is intended to be within the scope of the present disclosure. Other permutations and combinations that utilize one or more of the features/methods described herein are also possible, and such permutations and combinations are also considered part of the present disclosure without enumerating them specifically.

Notwithstanding the embodiments described above and shown in the accompanying drawing figures, various modifications and inclusions to those embodiments are contemplated and considered within the scope of the present disclosure.

As utilized herein with respect to numerical ranges, the terms "approximately," "about," "substantially," and similar terms generally mean+/−10% of the disclosed values, unless specified otherwise. As utilized herein with respect to structural features (e.g., to describe shape, size, orientation, direction, relative position, etc.), the terms "approximately," "about," "substantially," and similar terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

Connections between different components in communication with one another may be wired or wireless. In Figures referring to connectivity of two or more components in communication with one another show lines indicating the communication between components. By default, where these lines intersect, no contact is indicated, unless marked with a "●".

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

As used herein, the term "odorant" refers to one or more chemical compounds that may be present in a gaseous atmosphere. "Odorants" are not limited to chemical compounds capable of being detected by human olfactory capability. An odorant may be relevant in any scenario of importance to human health, public health, veterinary care, environmental safety, occupational safety, law enforcement or military operations, industrial production and may include toxins, pollutants, hormones, biological agents, viruses, particulates, fragrances, or any other chemical compound that may be detected by measuring the response of a sensor to its adsorption and/or desorption onto a sensor surface.

Although the figures and description may illustrate a specific order of method steps, the order of such steps may differ from what is depicted and described, unless specified differently above. Also, two or more steps may be performed concurrently or with partial concurrence, unless specified differently above.

It is important to note that any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A method for identifying one or more odorants, comprising:
exposing a sensor to one or more odorants to adsorb molecules of the one or more odorants onto the sensor surface, wherein the sensor comprises a quartz crystal resonator;

irradiating the sensor with a light sequence using two or more light sources to alter the adsorption kinetics of the molecules of the one or more odorants onto the sensor surface, wherein at least one of the two or more light sources is a broadband light source and light incident on the sensor comprises broadband light from the broadband light source, wherein the light incident on the sensor has a half-width at half-maximum of at least 10 nm;

measuring a change in one or more physical properties of the sensor during the irradiation due to adsorption of odorant molecules to the sensor or desorption of odorant molecules from the sensor, wherein the one or more physical properties comprises impedance of the quartz crystal resonator;

determining one or more characteristics of the one or more odorants based on the measured change during the irradiation.

2. The method of claim 1, further comprising inferring a property of a system from the one or more determined characteristics.

3. The method of claim 1, wherein determining the one or more characteristics comprises:

maintaining, by the one or more processors, a machine learning model trained using a training data set comprising measured changes in one or more properties of the sensor in response to adsorption of one or more known odorants during the light sequence; and determining, by the one or more processors, the one or more characteristics by applying the measured change in one or more physical properties of the sensor during the irradiation to the machine learning model.

4. The method of claim 1, wherein the light sequence comprises a first irradiation comprising light having a first light characteristic and a second irradiation comprising light having a second light characteristic; and wherein determining the one or more characteristics of the one or more odorants is based on a measured change of the impedance of the quartz crystal resonator during the first irradiation and a measured change of the impedance of the quartz crystal resonator during the second irradiation.

5. The method of claim 1, wherein the sensor comprises nanowires comprising NiO, $TiO_2$, ZnO, $SnO_2$, $WO_3$, $In_2O_3$, $VO_2$, $V_2O_5$, $Al_2O_3$, or combinations thereof.

6. The method of claim 1, wherein the two or more light sources comprise an infrared light source and an ultraviolet light source.

7. The method of claim 1, wherein the one or more characteristics of the one or more odorants comprises an identity of the one or more odorants or a concentration of the one or more odorants.

8. The method of claim 1, wherein the light sequence comprises a first irradiation with a first light source for a first duration of time, a second irradiation with a second light source for a second duration of time, and a third irradiation with the first light source and the second light source for a third duration of time.

9. The method of claim 1, wherein the light sequence is performed for more than one cycle.

10. The method of claim 1, comprising measuring a change in gain or a change in phase of the quartz crystal resonator due to adsorption of odorant molecules to the sensor or desorption of odorant molecules from the sensor.

11. The method of claim 10, wherein the impedance is measured in comparison to a fixed resistor.

12. The method of claim 1, wherein the one or more odorants is contained within sweat vapor from a human subject.

13. An olfactory sensor device, comprising:

a sensor configured to adsorb odorant molecules, wherein the sensor comprises a quartz crystal resonator;

two or more light sources configured to irradiate the sensor during exposure of the sensor to odorant molecules, wherein at least one of the two or more light sources is a broadband light source configured to emit broadband light incident on the sensor, wherein the broadband light incident on the sensor has a half-width at half-maximum of at least 10 nm;

one or more processors communicably coupled to the sensor and the two or more light sources, wherein the one or more processors are configured to:

operate the two or more light sources to produce a light sequence;

measure a change in one or more physical properties of the quartz crystal resonator in response to adsorption of odorant molecules to the sensor or desorption of odorant molecules from the sensor during the light sequence, wherein the one or more physical properties comprises impedance of the quartz crystal resonator; and identify one or more characteristics of the one or more odorant molecules by analyzing data associated with the measured change in one or more physical properties of the sensor.

14. The olfactory sensor device of claim 13, wherein the sensor comprises nanowires comprising NiO, $TiO_2$, ZnO, $SnO_2$, $WO_3$, $In_2O_3$, $VO_2$, $V_2O_5$, $Al_2O_3$, or combinations thereof.

15. The olfactory sensor device of claim 13, wherein the one or more light sources comprises an IR light source or a UV light source.

16. The olfactory sensor device of claim 13, wherein the one or more characteristics of the one or more odorants comprises an identity of the one or more odorants or a concentration of the one or more odorants.

17. The olfactory sensor device of claim 13, further comprising one or more auxiliary sensors in communication with the one or more processors.

18. The olfactory device of claim 13, wherein the device is wearable by a human subject.

19. The method of claim 1, wherein the light incident on the sensor has a half-width at half-maximum of at least 20 nm.

20. The olfactory device of claim 13, wherein the light incident on the sensor has a half-width at half-maximum of at least 20 nm.

* * * * *